(12) United States Patent
Tanaka et al.

(10) Patent No.: US 7,230,239 B2
(45) Date of Patent: Jun. 12, 2007

(54) APPARATUS FOR INSPECTING THREE DIMENSIONAL SHAPE OF A SPECIMEN AND METHOD OF WATCHING AN ETCHING PROCESS USING THE SAME

(75) Inventors: Maki Tanaka, Yokohama (JP); Hidetoshi Morokuma, Hitachinaka (JP); Chie Shishido, Yokohama (JP); Yuji Takagi, Kamakura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 479 days.

(21) Appl. No.: 10/918,381

(22) Filed: Aug. 16, 2004

(65) Prior Publication Data

US 2005/0048780 A1    Mar. 3, 2005

(51) Int. Cl.
*H01L 21/302* (2006.01)
*H01L 21/461* (2006.01)

(52) U.S. Cl. .................. 250/306; 250/310; 250/397; 250/307; 438/689; 73/105

(58) Field of Classification Search .............. None
See application file for complete search history.

(56) References Cited

OTHER PUBLICATIONS

"Electron beam testing handbook", a material of the 98$^{th}$ Study Group Meeting of the 132$^{nd}$ Committee of Application of Charged Particle Beams to Industries, Japan Society for the Promotion of Science.

*Primary Examiner*—Nikita Wells
*Assistant Examiner*—Zia R. Hashmi
(74) *Attorney, Agent, or Firm*—Antonelli, Terry, Stout & Kraus, LLP.

(57) ABSTRACT

A system for inspecting a pattern shape operates to detect secondary electrons from a specimen by irradiation of a focused electron beam and perform arithmetic processing on this detected signal. The detected signal waveform is divided into a plurality of regions on the basis of a variation of the signal quantity. The size of the divided regions is used for quantitative evaluation of a three dimensional shape of the specimen. This system, especially by displaying measurement results of the pattern shape for each divided signal waveform (bottom width in the final shape, resist bottom width, etching shift quantity, and etching slope-angle component by the exposure), permits an easy check on which a component varies and how the component varies in all shape variations. With this arrangement, a pattern cross section information effective in determining etching process conditions can be acquired using images by an in-line SEM capable of nondestructive observation.

23 Claims, 31 Drawing Sheets

Normal

Upward taper

Side-wall slope angle $\theta$

Downward taper

Flaring

Poly Si

SiO$_2$ (Gate oxide film)

Si Substrate

FIG.3A
After exposure
FIG.3B
BARC etching
FIG.3C
Poly Si etching
Step 1
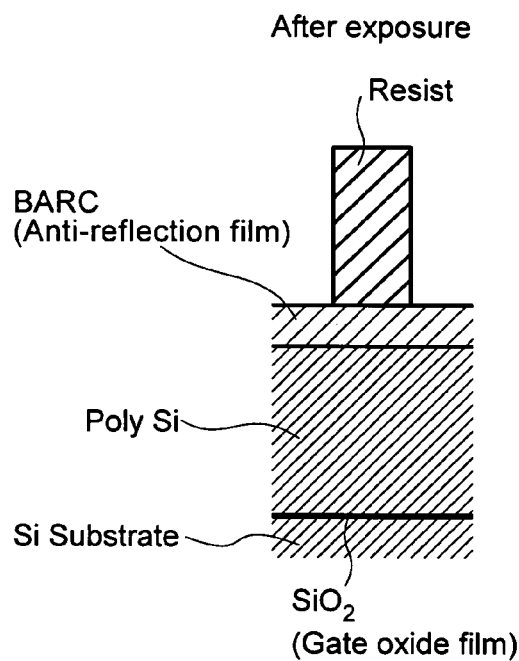
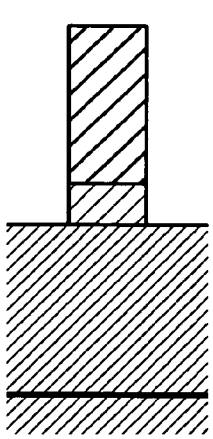
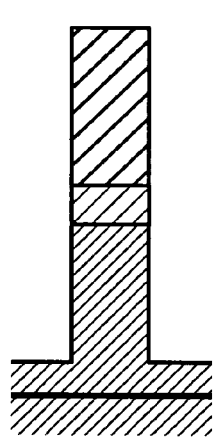
FIG.3D
Poly Si etching
Step 2
FIG.3E
Resist removal
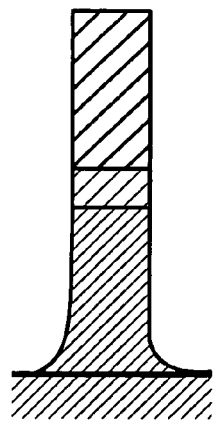
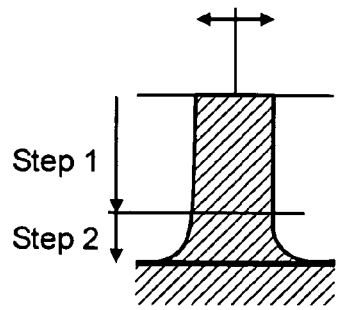

Maximum slope point for each slope

Size th=min+(max−min) × a
a:Predetermined ratio (0.0−1.0)

max
th
min
Size

SLOPE LINE   SLOPE LINE
EDGE   EDGE
BASE LINE   BASE LINE
Size

Upward taper

Upward Taper with flaring

Distance from wafer center

707
CD bias

705
Etching shift
quantity

708
Material A
Slope-angle
component

709
Material B
Slope-angle
component

700 Scale

Material A
Material B

APPARATUS FOR INSPECTING THREE DIMENSIONAL SHAPE OF A SPECIMEN AND METHOD OF WATCHING AN ETCHING PROCESS USING THE SAME

BACKGROUND OF THE INVENTION

The present invention relates to a technology that is directed to a method and system of evaluating the quality of a processed shape of a circuit pattern formed on a wafer using an electron beam image of the circuit pattern in the manufacture of semiconductor devices.

The present inventors have determined that the following technologies exist with regard to evaluating the quality of a processed shape of a circuit pattern formed on a wafer.

In order to obtain the desired processing performance in an etching process, for example, a supporting experiment is normally carried out in advance. The experiment is performed with a plurality of processing conditions being set as parameters, and processing conditions considered optimum are determined and registered as a recipe in the etching equipment. In this operation of optimum condition finding, the quality of etching performance is checked mainly by cross sectional observation of the pattern.

FIGS. 2A to 2B show examples showing a difference in a pattern cross section after the etching. FIGS. 2A to 2D are sectional views of gate wiring, showing examples of how this shape may change with process conditions. Generally in the gate process, shape control of a bottom part is very important. This is because the shape of the pattern bottom affects the results of a subsequent ion implantation process, and the size itself of the pattern bottom largely affects the characteristic of a device. FIG. 2A shows a shape that is generally considered most desirable, in which the slope angle of the pattern side wall is almost vertical, and flaring and other defects are not formed at the pattern bottom. On the contrary, the upward taper shown in FIG. 2B, the downward taper shown in FIG. 2C, and the flaring shown in FIG. 2D are shape abnormalities occurring from improper process conditions. It is necessary to realize the state of FIG. 2A by alteration of the processing conditions.

Next, an outline of a gate etching process and the relationship between a final shape and the processing conditions will be described with reference to FIGS. 3A to 3E. In this process, a film to be processed is subjected to etching based on a resist pattern formed in a photolithographic process. Generally, in superfine processes in recent years, it is often the case that a BARC (Bottom Anti-Reflective Coating: a reflection reducing coating at the time of exposure) is formed under the resist. FIGS. 3A to 3D are directed to such a case. Here, a case of one step of BARC etching and two steps of Poly Si etching are considered. There is also a case where BARC is processed through much more steps than this case.

After the exposure, as shown in FIG. 3A, the BARC layer is disposed on the film to be processed (in FIG. 3, Poly Si film), and the resist pattern is formed on it. In a normal production line, the size of the resist pattern is measured at this state, and whether there is an abnormality in the exposure process is checked. In the subsequent etching process, first, the BARC layer is etched (FIG. 3B). Next, Poly Si etching is performed using the resist and the pattern of the BARC film as a mask with etching conditions switched. At this time, normally the etching of the Poly Si film is processed in several sub-steps constituting the etching. First, the etching is performed vertically under conditions having relatively high anisotropy (in FIG. 3C, Poly Si etching Step 1). Next, when approaching the lower end, the conditions are switched to those having high selectivity (in FIG. 3D, Poly Si etching Step 2) so that the etching may not break through the oxide film or introduce damage, and then the etching is processed to an underlayer oxide film by making some sacrifices in terms of anisotropy. These steps of processing shown in FIGS. 3B to 3D are performed continuously by changing the conditions in a single piece of etching equipment. After the etching process, a resist removal process by ashing and washing is performed to form a gate pattern, as shown in FIG. 3E. In this series of processes, several conditions are switched. Thus, it is necessary not only to check for the presence of abnormalities, but also to determine a problem-causing step in evaluation of a processed result using sectional photographs. Condition optimization of each step is carried out by conducting, for example, the following judgments: if there is an abnormality in the slope angle of the side wall, Step 1 of the Poly Si etching is a main cause; and, if the flaring deteriorates the processed shape, Step 2 of the Poly Si etching is bad.

When the processing conditions are determined by this operation of optimum condition finding, they are registered in a recipe of the etching equipment and the etching process will be performed on the basis thereof in an actual production line. It is ideal that the etching performance at this time is exactly the same as that when the optimum condition finding is performed in advance. However, an increase/decrease of the etching rate and the like may occur due to the state of the inner wall of an etching chamber, an atmospheric change with the lapse of time, etc. Along with higher integration of the LSI in recent years, a processing performance that supports more minute processing dimensions and a higher aspect ratio is being required, and, accordingly, high-accuracy process control for a difference of a shape is desired to cope with process variations like this. At present, variation in the processed pattern shape resulting from variation of these etching conditions is detected by size measurement with a measuring SEM, or by acquiring SEM images having different slope angles and measuring its three dimensional shape by a principle of stereoscopy.

With respect to the technologies for evaluating the quality of the processed shape of a circuit pattern formed on the wafer, as described above, the present inventors have determined the following.

For example, in the conventional finding of optimum etching conditions, as described above, the quality of the processed shape is checked by cross sectional observation of the pattern. However, this check of the cross section is carried out by cleaving the wafer and observing it using a cross sectional SEM or the like, which takes a considerably long time; therefore, efficient finding of optimum conditions is rather difficult. Preparation of specimens for cross sectional observation and observation work require skills different from those used in the optimum etching condition finding and suffers from a high cost. The preparation is a destructive evaluation, so wafers after the observation need to be discarded. In order to conduct process control as well as condition finding, it is mandatory to evaluate a shape nondestructively. On the contrary, dimensional measurement by the measuring SEM makes it easy to conduct measurement nondestructively, but provides only a difference in a pattern size. Therefore, there is a problem in that information sufficient to set up the conditions of the etching process cannot be obtained.

The following description identifies problems associated with shape evaluation (size measurement) by the conventional SEM, which constitute technological problems that the present invention intends to solve.

It is common to conduct dimensional measurement by means of a measuring SEM using line profiles of secondary electron images. Thus, at first, we will review a common relationship between a cross section and a line profile of secondary electron intensity that is described in "Electron beam testing handbook", p. 261, a material of the 98th Study Group Meeting of the 132nd Committee of Application of Charged Particle Beams to Industries, Japan Society for the Promotion of Science.

FIG. 4 shows the following:

(A) When the electron beam is irradiated onto the substrate part, the intensity of the detected secondary electron signal shows a constant value that depends on the emission efficiency of secondary electrons of the substrate material.

(B) When the beam irradiating point approaches the pattern, secondary electrons among the generated secondary electrons that collide with the slope part of the pattern increase and the capture efficiency of secondary electrons decreases, whereby the signal intensity lowers slightly.

(C) Secondary electron signal intensity exhibits a minimum in a position that shifts from the bottom edge of the pattern outward by a half of the beam diameter.

(D) After passing point C, the signal intensity increases rapidly almost linearly due to a change in secondary electron emission efficiency that corresponds to a change in the slope angle of the specimen.

(E) As the beam irradiation point approaches the top edge, the increase of the signal intensity becomes mild because each irradiation point on the slope part has a different capture efficiency of the emission secondary electrons.

(F) The secondary electron signal intensity exhibits a maximum in the position that shifts from the top edge of the pattern outward by a half of the beam diameter.

(G) The secondary electron signal intensity decreases after passing point F, and settles to a fixed value that is determined by the secondary electron emission efficiency of the pattern material.

Although FIG. 4 shows the case of a photoresist, the behavior is also the same in the case of other materials.

In order to measure the size from such a line profile, it is necessary to detect an edge position of the pattern from the line profile. As a method of detecting an edge position whose program is loaded on the measuring SEM, the following methods are known: a method of detecting a maximum slope-angle position (maximum gradient method), as shown in FIG. 5A; a threshold method of detecting an edge position using a predetermined threshold value, as shown in FIG. 5B; a line approximation method in which the edge parts and a base material part are approximated by straight lines and cross points of these lines are detected, as shown in FIG. 5C; and other methods.

However, with methods of FIG. 5A and FIG. 5B, it is impossible to know correctly which height in an actual cross section of the pattern is chosen for measurement of the size between the points determined by the height. As shown in FIGS. 2A to 2D, since the problem of the etching process is a difference in the pattern shape, a technique is needed that can make clear which height is chosen for detection of the edge positions. With a sample having such a waveform as shown in FIG. 4, it is possible to measure approximately the size of the pattern bottom part by the straight line approximation method of FIG. 5C. However, it is not necessarily possible to obtain correct measured values depending on its shape. That is, since the secondary electron signal quantity of an SEM depends on the slope angle of a pattern surface, in the case where the slope angle varies at the pattern side wall, the waveform does not become a straight line; therefore, the straight line approximation method becomes incapable of measuring correct sizes. Mere measurement of either the width of the pattern top part or the width of the bottom part cannot lead to correct evaluation of the state of the etching process. This is because, as shown in FIGS. 3A to 3E, in order to ascertain which step causes a problem, shape information corresponding to each of the steps is required. Even if a three dimensional shape inspection technique is employed that uses stereoscopy and is effective in acquiring three dimensional information, it is difficult to sufficiently obtain information useful for optimum etching condition finding. In order to perform stereoscopy, it is necessary to determine points of the image between two or more images whose beam irradiation angles are different. However, in the case where the pattern shape varies continuously and smoothly, as in the bottom part of the pattern of FIG. 3E, appropriate corresponding points cannot be obtained. This causes a problem in that sufficient evaluation cannot be performed.

SUMMARY OF THE INVENTION

The gist of the present invention resides in acquiring information of a pattern cross section effective in determination of etching process conditions using an image of an inline SEM capable of nondestructive observation. In terms of that, the conventional methods fall short of this goal. The invention realizes an effective method of finding process conditions and a method of watching processes by acquiring information of a cross section by an SEM, which enables measurement of a cross section relatively easily and nondestructively, instead of conducting costly cross sectional observation.

The primary aspect of the invention is directed to an apparatus that comprises electron-beam irradiating means for irradiating a focused electron beam onto a specimen while scanning the electron beam, signal detecting means for detecting secondary electrons generated from the sample by irradiation of the electron beam, and signal processing means for processing signals from the signal detecting means. With this configuration, the apparatus quantitatively evaluates a three dimensional shape of the specimen by processing a signal waveform obtained from the signal detecting means. The invention also enables quantitative estimation of a cross section of a concavity-and-convexity pattern formed on the surface of the specimen.

In particular, the invention permits an operator to easily check which component varies and how the component varies among variations of the whole shape by displaying measurement results of the pattern shape for each divided signal waveform, respectively. A specific description will be given.

With respect to two or more kinds of shape-representing values selected from the group consisting of sizes of plural divided regions and values obtained by summing or subtracting the sizes of the plurality of divided regions, wafer maps each representing a distribution in a wafer plane are prepared, respectively. And, these maps are displayed in an arrangement or in a switch-selectable manner. Alternatively, the apparatus calculates two or more kinds of shape-representing values for plural specimens processed by the same processing equipment, under the same processing conditions, but at different times. And, time variations of these two or more kinds of shape-representing values are graphically displayed.

In another aspect, the invention makes it possible to determine optimum etching process conditions and carry out process watching by mapping the information of the three dimensional shape of the pattern that was evaluated or estimated, as described above, thereby grasping a relationship between the pattern shape and the etching conditions quantitatively.

In another aspect, the invention makes it possible to evaluate the pattern shape similarly and determine etching process conditions and carry out process watching, also through pattern shape evaluation that uses tilt images and reflection electron images.

According to the invention, the dimensional shape of a semiconductor circuit pattern can be evaluated easily and nondestructively. As a result, it becomes possible to considerably improve the efficiency of processing condition finding that has hitherto been carried out by cross sectional observation. In addition, it becomes possible to easily carry out the processing condition finding that has hitherto depended on experience and intuition based on quantitative evaluation results. Furthermore, the invention enables detection of a three dimensional abnormality that might have been overlooked in the conventional dimensional measurement and, consequently, can prevent defects in the etching pattern, that cannot be reproduced, from being included in the products. Furthermore, high-accuracy process control becomes possible and it becomes possible to provide a stable etching process.

These and other objects, features and advantages of the invention will be apparent from the following more particular description of preferred embodiments of the invention, as illustrated in the accompanying drawings.

BRIEF DESCRIPTION OF THE DRAWINGS

FIGS. 2A to 2D are cross-sectional views in which FIG. 2A shows a normal pattern, FIG. 2B shows an upward taper, FIG. 2C shows a downward taper, FIG. 2D shows flaring.

FIG. 3A shows a resist pattern cross section after an exposure step; FIG. 3B is a cross section showing the resist pattern after the BARC etching; FIG. 3C is a cross section showing the resist pattern after the first step at which the Poly Si film is etched; FIG. 3D is a cross section showing the resist pattern after the second step at which the Poly Si film is etched; and FIG. 3E shows a cross section after the removal of the resist.

DESCRIPTION OF THE PREFERRED EMBODIMENTS

Figure 1:
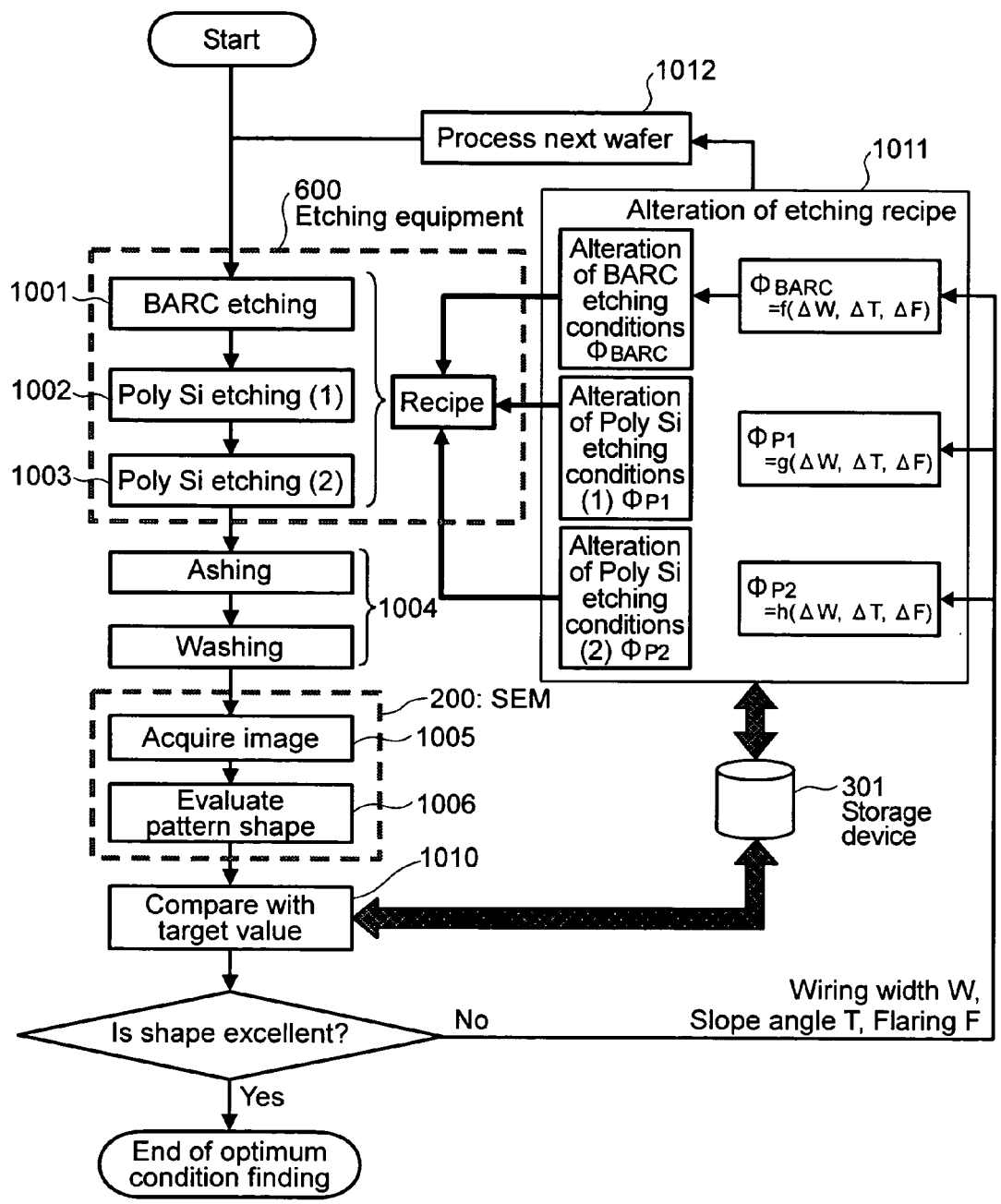
FIG. 1 is a block diagram which shows a procedure for finding optimum etching conditions in a second embodiment of the invention.

Hereafter, various embodiments of the present invention will be described in detail referring to the drawings. Note that in all the figures, any member having the same function is in principle designated with the same reference numeral, and a repeated explanation therefor will be omitted.

Figure 6:
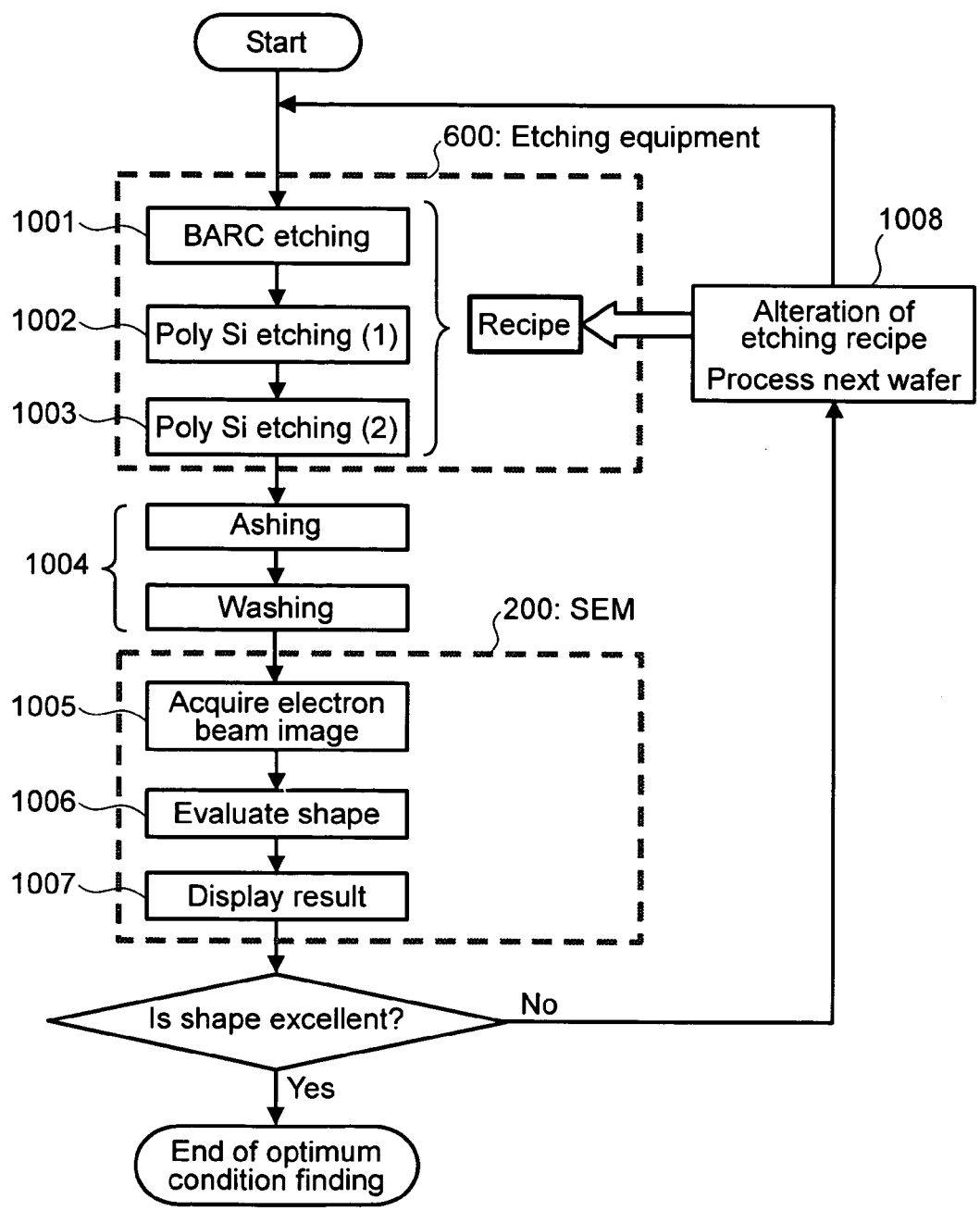
FIG. 6 is a flow diagram showing a procedure for finding an optimum etching condition representing a first embodiment of the invention.
Figure 7:
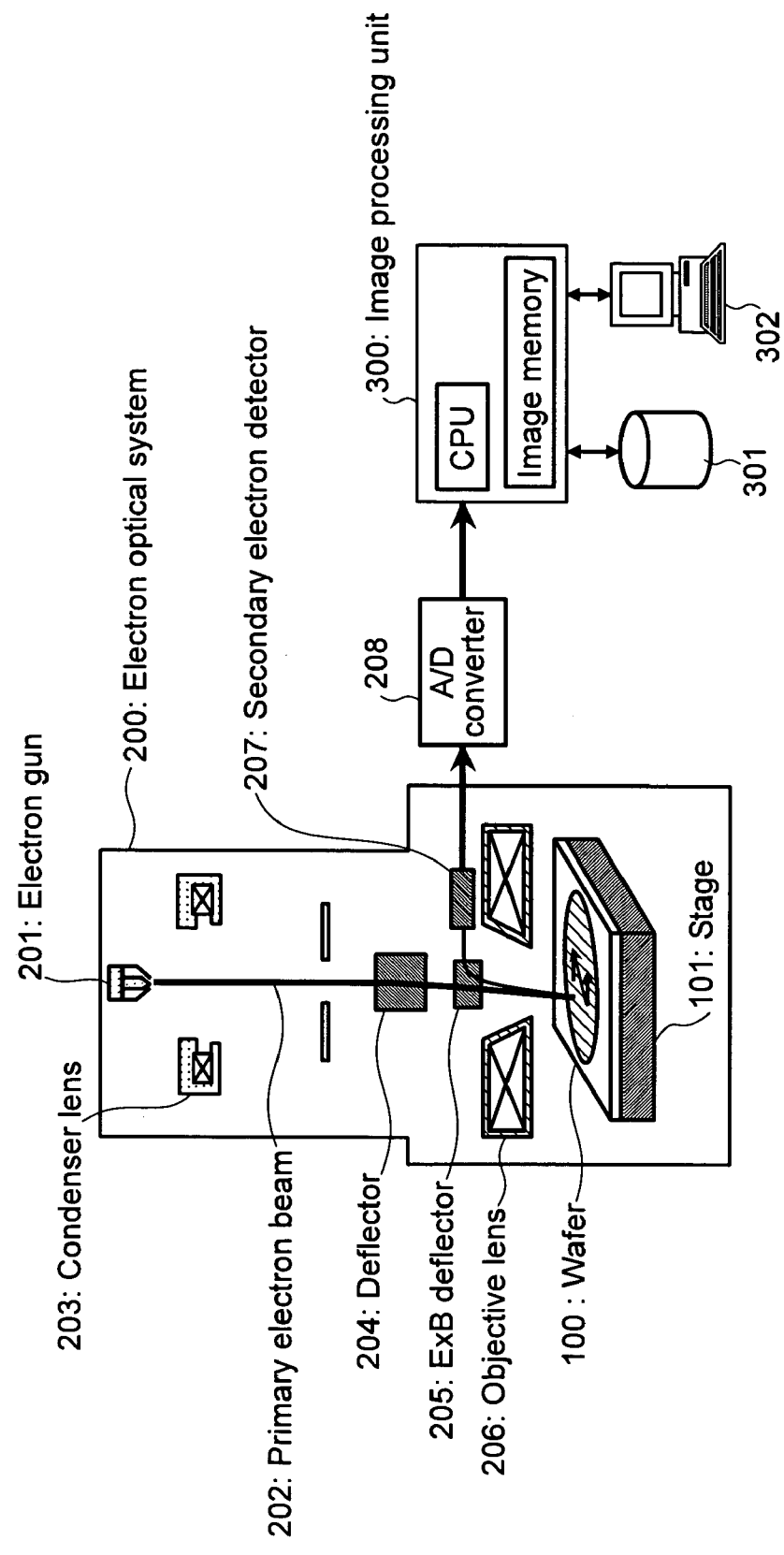
FIG. 7 is a diagram showing the overall configuration of a CD-SEM according to the first embodiment of the invention.

FIG. 6 is a conceptual diagram of a procedure showing optimum etching condition finding that uses a pattern shape evaluation system built on a measuring SEM (a schematic configuration is illustrated in FIG. 7) according to a first embodiment of the invention. In this embodiment, first, an etching process consisting of BARC etching (Process 1001), Poly Si etching (1) (Process 1002), and Poly Si etching (2) (Process 1003) and a resist removal process (Process 1004) consisting of ashing and washing are performed on a wafer to form a pattern on it. Here, Processes 1001 to 1003 are continuously performed inside the same etching equipment 600. Next, an electron beam image of a circuit pattern after the etching is acquired using a measuring SEM (Process 1005). Subsequently, the shape of the pattern is evaluated using electron beam images (Process 1006), and the obtained result is displayed on a screen (Process 1007). Based on the obtained evaluation result, the operator evaluates the quality of the pattern shape. If an excellent shape is not obtained, a step in which processing conditions are altered is determined and new conditions are set up based on the obtained information of a three dimensional shape (Process 1008). A method of acquiring information concerning the cross section will be described in detail separately.

FIG. 7 is a block diagram showing the configuration of a measuring SEM 200 used in this pattern shape evaluation system. In FIG. 7, a primary electron beam 202 emitted from an electron gun 201 is converged with a condenser lens 203, passes through a beam deflector 204, an ExB deflector 205, and an objective lens 206, and is irradiated onto a wafer 100 placed on a stage 101 so as to focus on it. On irradiation with the electron beam, secondary electrons are generated from the wafer 100. The secondary electrons generated from the specimen wafer 100 are deflected by the ExB deflector 205 and detected by a secondary electron detector 207. A two-dimensional electron beam image is obtained by two-dimension scanning of the electron beam by the deflector 204, or by repeated scanning of the electron beam in the X-direction by the deflector 204 together with detection of electrons generated from the specimen in synchronization with continuous movement of the wafer in the Y-direction by means of the stage 101.

The signal detected by the secondary electron detector 207 is converted into a digital signal by an A/D converter 208 and sent to an image processing unit 300. The image processing unit 300 has an image memory for storing digital images temporarily and a CPU for calculating a line profile and features from images in the image memory. It has a storage device 301 for storing detected images, or line profiles, or information of calculated pattern shapes, etc. A display device 302 is connected to the image processing unit 300, enabling the operator to perform necessary operations of the device, checking of the detected result, etc. with a graphical user interface (hereinafter referred to as GUI).

Figure 8:
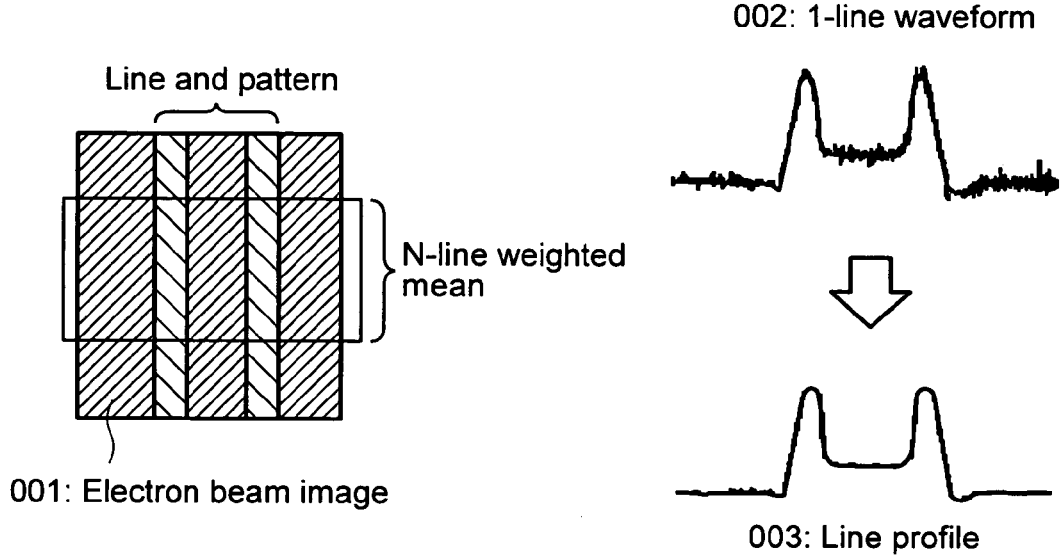
FIG. 8 is an explanatory diagram showing line-profile processing according to the first embodiment of the invention.

Next, a procedure for calculation of the information of a three dimensional shape performed by the image processing unit 300 will be described with reference to FIG. 8 through FIG. 11. First, as shown in FIG. 8, in order to improve the S/N, a smooth line profile 003 is formed by N-line averaging of 1-line waveform 002 for the acquired electron beam image 001. This line profile 003 shows the signal quantity depending on the shape of the pattern side wall. Details of the relationship between this signal quantity and the pattern cross section will be described with reference to FIG. 9.

Figure 4:
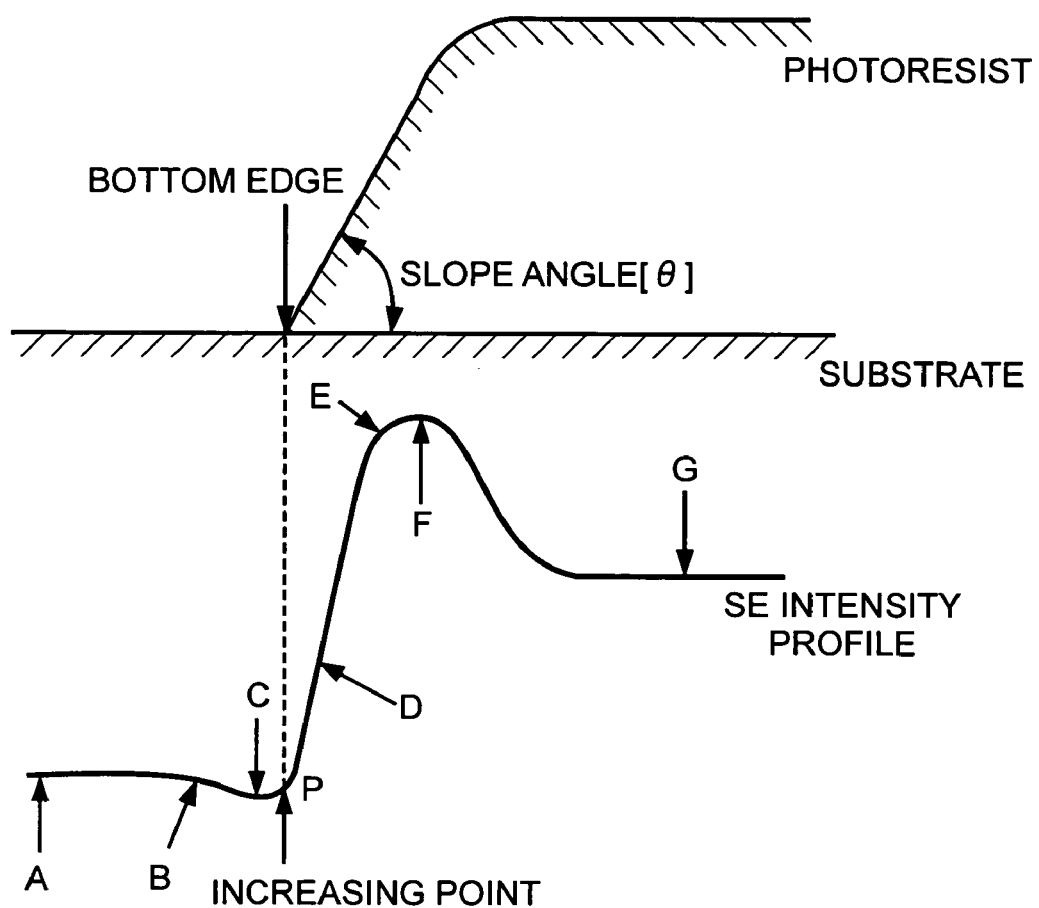
FIG. 4 is a diagram showing a relationship between the cross section of the resist and the secondary electron signal intensity.
Figure 9A:
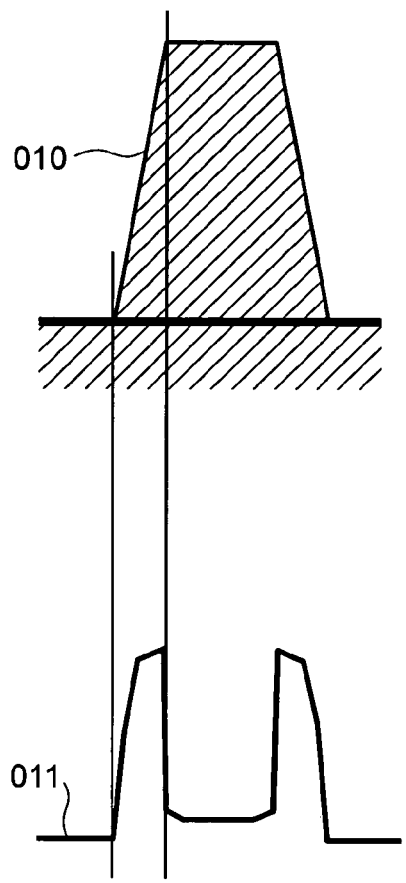
FIG. 9A is a diagram showing a line profile of an SEM image in the case of an upward tapered cross section.
Figure 9B:
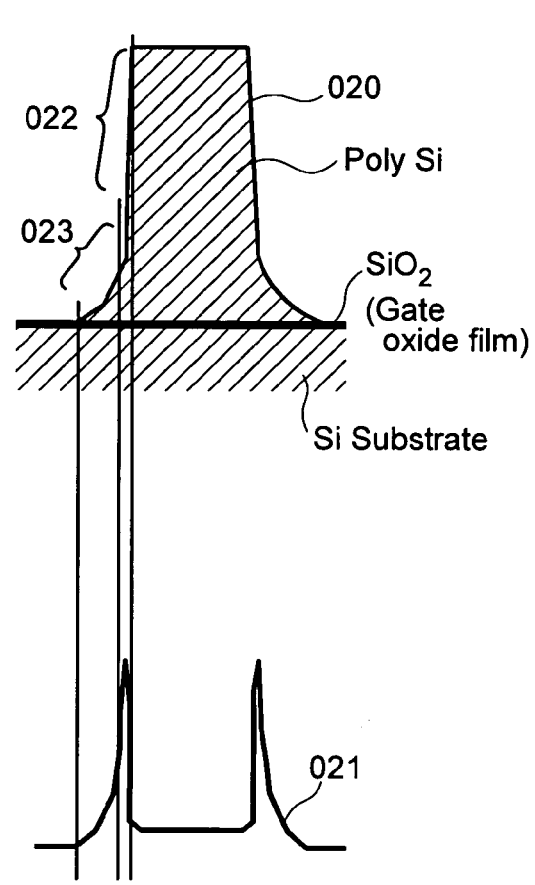
FIG. 9B is a diagram showing a line profile of an SEM image in the case of an upward tapered cross section with flaring.

As explained with reference to FIG. 4, the signal quantity varies depending on the slope angle of the side wall; and, when the beam is shifted from the top edge of the pattern outward roughly by a half of the beam diameter, the signal quantity of secondary electrons exhibits a maximum. It is known that the signal quantity of secondary electrons increases in proportion to $1/\cos\theta$, where $\theta$ denotes the slope angle. For this reason, as shown in FIG. 9A, if the cross section 010 has no flaring and the whole side wall maintains a relatively high slope angle, the line profile 011 increases abruptly from the bottom edge. However, as shown in FIG. 9B, when the cross section 020 has a flaring, the flaring section 023 provides a small signal quantity of secondary electrons as compared to an upper part that has a relatively high slope angle section 022. Using this characteristic, information of the cross section is acquired by the following procedure. First of all, by dividing the cross section into a section with relatively small signal quantity and a section with relatively large signal quantity, the SEM image observed from the top of the specimen is divided into a high slope angle section 022 and a low slope angle section 023 using only the SEM image.

Figure 10:
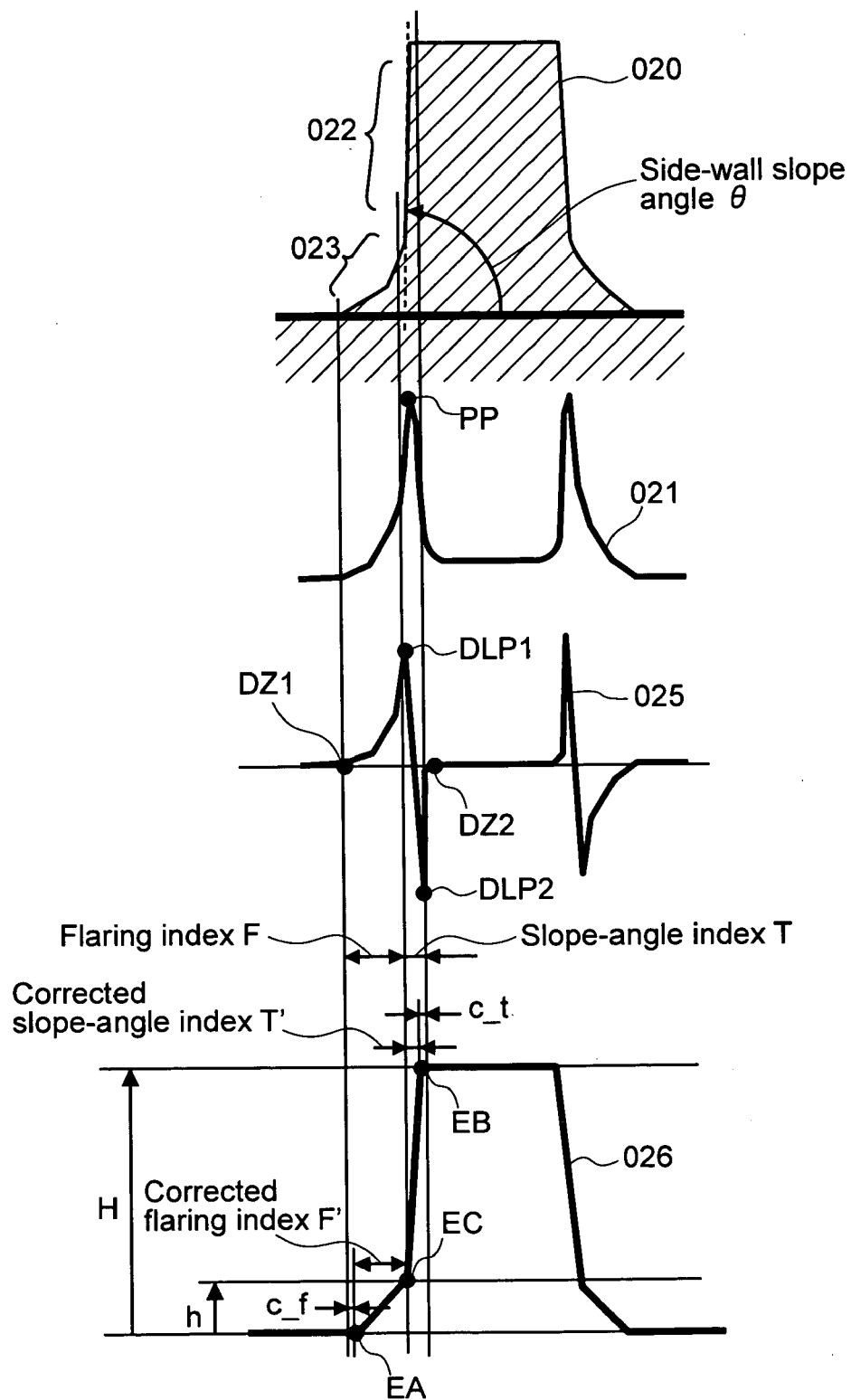
FIG. 10 is a diagram showing a three dimensional shape index calculating method according to the first embodiment of the invention.
Figure 11:
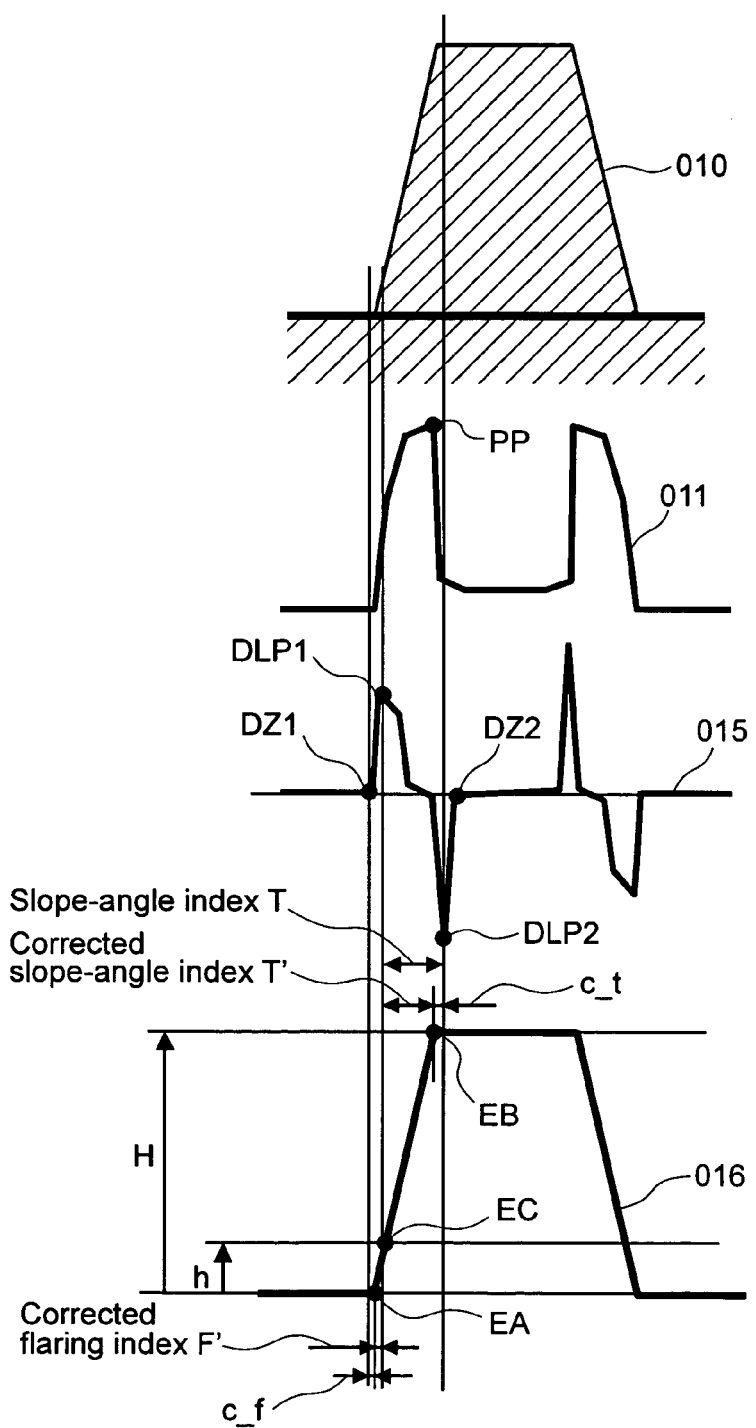
FIG. 11 is a diagram showing a three dimensional shape index calculating method according to the first embodiment of the invention.

FIG. 11 provides a detailed illustration of FIG. 9B, and FIG. 11 is the same of FIG. 9A. As shown in FIG. 10, formation of the first differential waveform 025 of the obtained line profile 021 provides a waveform having extrema (DLP1, DLP2) at locations where the brightness changes abruptly in the original line profile 021. For this reason, a section between these local extrema DLP1 and DLP2 corresponds to a section having a relatively high slope angle 022 in the side wall. Then, the distance between these extrema is designated as an index T of the slope angle. On the other hand, since a region extending from an outside extremum (DLP1) of the differential waveform at the edge part to a point where the differential waveform becomes zero (DZ1), namely a point whose brightness becomes identical to that of an underlayer, represents a flaring section whose slope angle is relatively low, the distance of these points is designated as an index F of the flaring.

As with FIG. 10, FIG. 11 shows indexes obtained for the shape of FIG. 9A. As can be understood from a comparison between FIG. 10 and FIG. 11, the slope-angle index T is proportional to tan (π−θ) provided that the pattern height H is constant, taking a smaller value as θ approaches the vertical (90°). In the case of a downward taper, information of the side-wall section disappears, and only a piece of information resulting from the edge effect is detected; therefore, the slope-angle index T stays at a constant value. Contrary to this, a flaring index F takes a larger value with increasing flaring. Thus, from these indexes, information of a three dimensional shape of the pattern that is important especially in the etching process can be obtained.

Moreover, a coarse cross section of the pattern can be estimated using these indexes. First, the indexes of T and F are subjected to the following correction considering the edge effect and the resolution of the SEM images.

$$T'=T-c\_t \quad \text{(Formula 1)}$$

$$F'=F-c\_f, \quad \text{(Formula 2)}$$

where c_t and c_f in Formula 1 and Formula 2 are constants, c_t in Formula 1 is a width that is observed even if the side wall is completely vertical. This value is mainly determined by the edge effect of the pattern top part, and shall be measured in advance with an appropriate sample. c_f of (Formula 2) is an offset component observed even when there is no flaring. This value mainly depends on the resolution of the SEM image, such as a beam diameter of the primary beam, a distribution of secondary electrons generated inside the object.

Figure 5A:
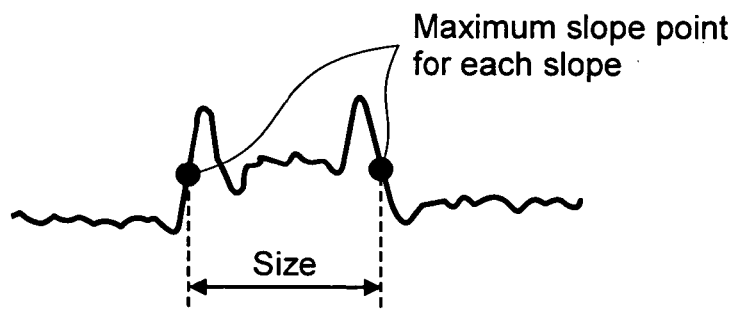
FIG. 5A is a diagram showing a method of finding a pattern size from the maximum slope points in slopes of a line profile.
Figure 5B:
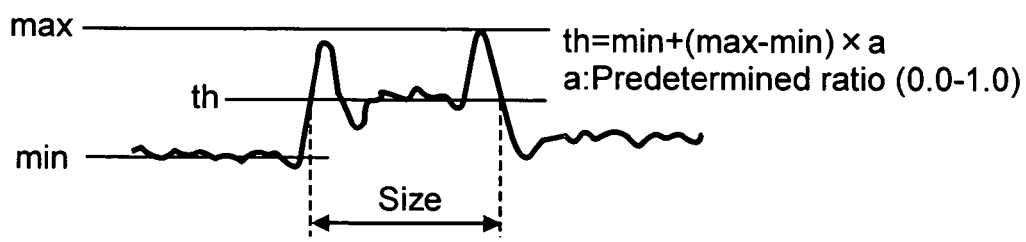
FIG. 5B is a diagram showing a pattern size from the maximum and the minimum of the line profile signal.
Figure 5C:
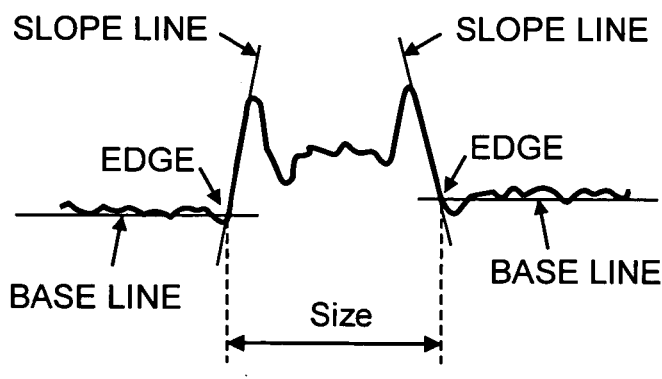
FIG. 5C is a diagram showing a method of finding a pattern size from intersections between the slope line of the line profile and the base line.

Using T' and F' in these formulas, point EA that exists outside an outside peak DLP1 of the first differential waveform by the amount F' with zero height (same level as the underlayer) and point EB that exists inside the outside peak DLP1 by the amount T' with height H (same level as the upper surface of a film to be processed) are determined. Since the thickness (H) of this film to be processed that is a target of etching is controlled by using a thickness gauge etc. with high accuracy in a normal production line, H can be treated as a known value. For a value of H, a measurement result of a wafer to be inspected that was actually measured by the thickness gauge may be used, or a specification value at the time of film formation may be used. Next, an appropriate height h is assumed and point EC with a height h on the reference point (DLP1) is determined. By connecting these points EA, EB, and EC, as shown in FIG. 10 and FIG. 11, a rough pattern cross section can be estimated. Here, h represents a height corresponding to a switchover point of etching conditions that was explained in conjunction with FIGS. 3A–3E. What is necessary for h is to investigate its coarse value from an etching rate at each step and a processing time that is set in the recipe or the like. However, it does not need to be such a correct value. Even if an exact height h of point EC is not known, information sufficient for determination of a problematic step and its countermeasure can be obtained Furthermore, in the conventional measurement system shown in FIG. 5, which points on the pattern are used to find the width could not be determined. Contrary to this, if point EB shown in FIG. 10 or FIG. 11 is found in the right and left edges, the top-part width can be found from their distance. Similarly, if point EA is used, the bottom-part width can be found; if point EC is used, a rough width of the taper bottom except for the flaring can be found. Thus, with the use of the system of the invention, a pattern size in a desired position can be measured with high accuracy. Once the wiring width can be measured correctly, the size transformation difference with respect to the resist pattern after the exposure that has been measured in advance can be grasped correctly. In the case where the etching is performed at the steps shown in FIGS. 3A–3E, it is often the case that the size transformation difference when a resist pattern is transformed from the resist pattern to the top-part size after the etching is adjusted by the BARC etching (this is because the BARC film is of the same organic material as the resist, and hence the resist can be etched at the time of BARC etching). Therefore, if the top-part size is measured correctly, it becomes possible to make the BARC etching conditions optimum.

Figure 2A:
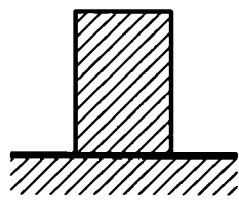
Figure 2B:
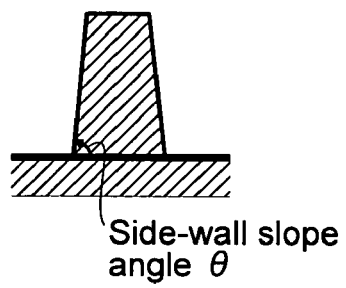

If a rough pattern shape is grasped in this way, the operator becomes able to set up the etching conditions for realizing a desired shape, as seen in FIG. 2A, efficiently.

As information of a three dimensional shape used in finding the optimum etching conditions, the flaring index F (or F'), the slope-angle index T (or T'), pattern sizes of the top and bottom parts, etc. may be used, as they are, in addition to estimated shapes 026, 016 shown in FIG. 10 or FIG. 11, or a result of calculation of the slope angle θ from the slope-angle index T may be displayed and the operator is allowed to use it. If a pattern cross section specified by the indexes has been brought into correspondence with the steps of the etching process shown in FIGS. 3A–3E, what is necessary is to alter only conditions of a corresponding step so that indexes come to values specifying the desired shape.

Incidentally, the side-wall slope angle θ can be found by the following Formula 3.

$$\theta=\pi/2-a\,\tan(T'/H) \quad \text{(Formula 3)}$$

In the above-mentioned embodiment, the signal waveform is divided into a high slope angle part and a low slope angle part using the first differential value thereof. However, if the region of the profile waveform is divided on the basis of a value of the signal quantity itself using an appropriate threshold, the same effect can be obtained.

Figure 12A:
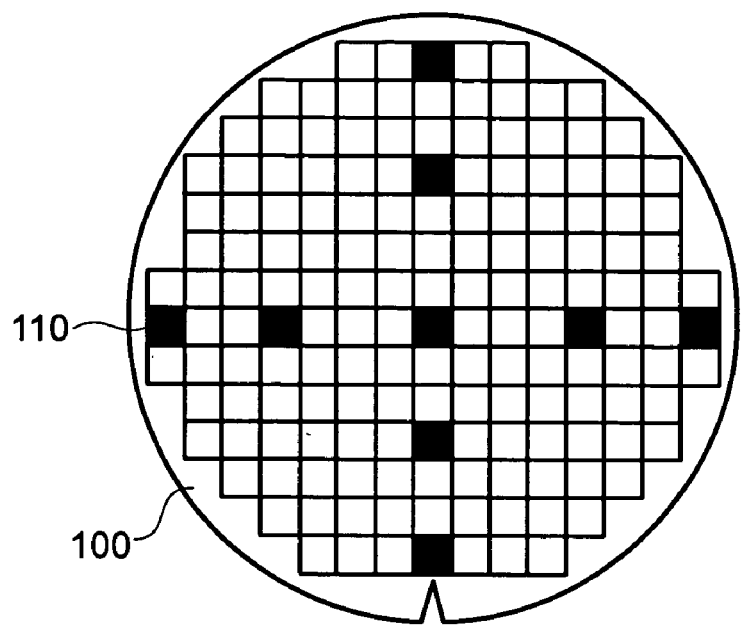
FIG. 12A is a diagram which shows three dimensional shape index acquiring locations in the first embodiment of the invention.
Figure 12B:
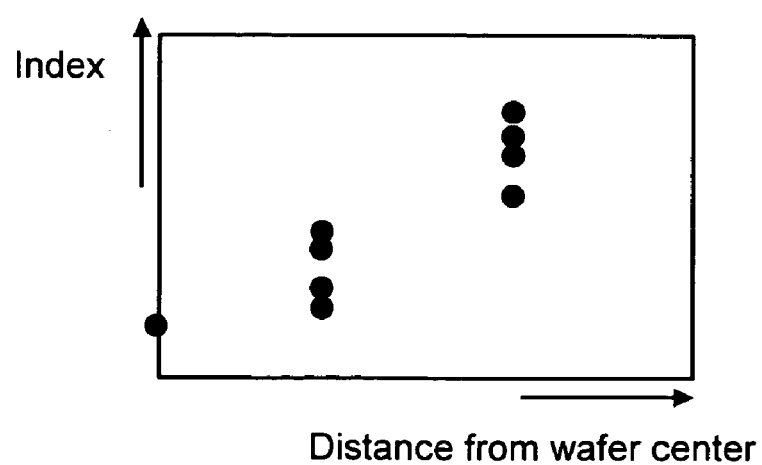
FIG. 12B is a diagram which shows a method of displaying location dependency of a three dimensional shape index.

Next, a location at which this pattern shape evaluation after the etching is executed will be described with reference to FIGS. 12A and 12B. In etching equipment, since it is often the case where uniform processing performance of etching cannot be obtained depending on a location in the wafer due to an effect of plasma density distribution etc. in the etching chamber, the uniformity in the wafer plane becomes an important item in the optimum etching condition finding. Then, it is effective to measure information of the pattern shape in several points in the plane of the wafer 100 by the method described above and to display their variations intelligibly, as shown in FIG. 12A. FIG. 12A shows an example of evaluation locations in the wafer plane. For example, if the shape evaluation is performed in evaluation target chips 110 painted black (total 9 chips in FIG. 12A), a shape distribution in the wafer plane can be found. In the etching process, since it is often the case that a state varies in a concentric circle manner in the wafer plane, if the shape indexes are graphically displayed as a function of a distance from the wafer center, as shown in FIG. 12B, the state of the processed wafer can be checked easily. Similarly, since the shape may change due to the influence of pattern density, location dependency of the shape in a chip may be displayed by measuring it at a few locations in the chip.

Figure 13:
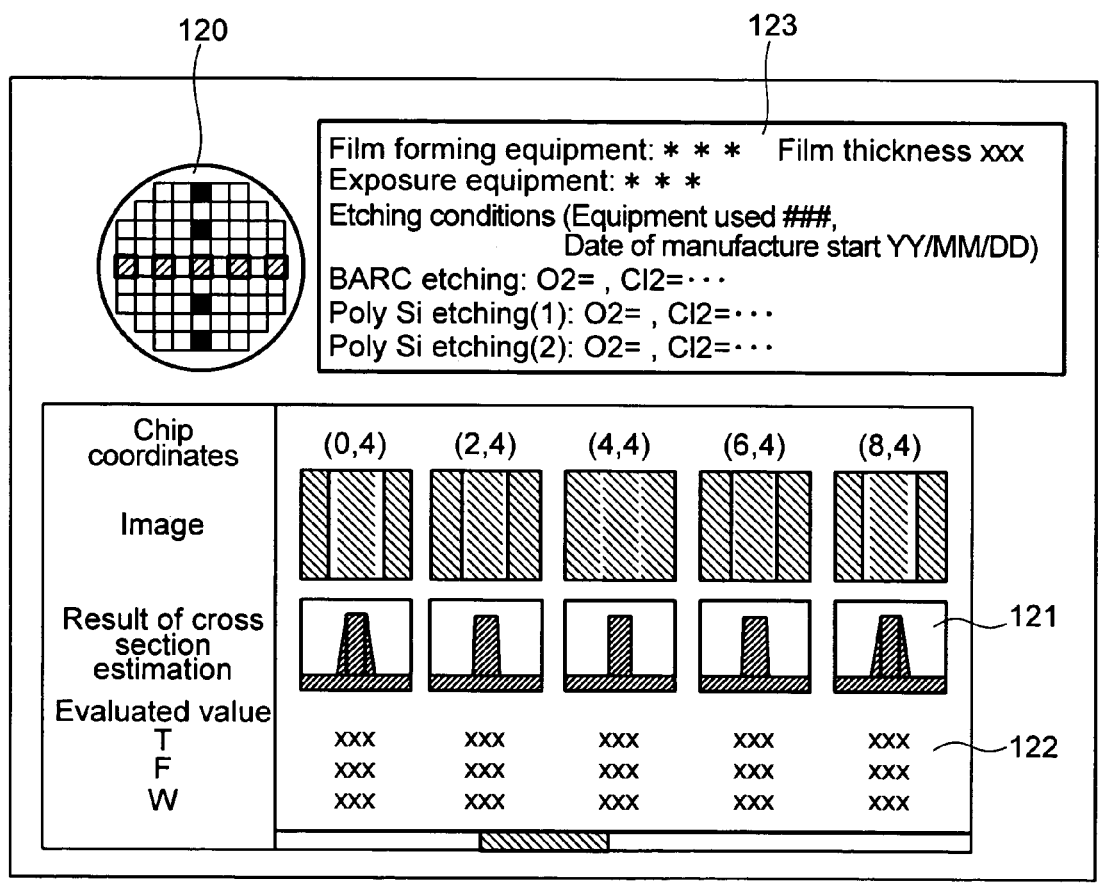
FIG. 13 is an explanatory diagram showing a display method of an acquisition result of information of a three dimensional shape in the first embodiment of the invention.

Next, an embodiment of result display for checking these results of shape evaluation will be described. FIG. 13 shows an example in which shape variation in the wafer plane is displayed using estimated cross sections. That is, the chips that underwent shape evaluation by acquisition of the image are displayed on a wafer map 120, and results of cross section estimation 121 and the three dimensional indexes 122 that correspond to respective chips are displayed. At this time, if an order of result display can be re-arranged according to a chip number or a distance from the wafer center etc., it is further preferable. As shown in FIG. 12B, a graph showing a relationship between the index and the location in the wafer plane may be displayed for each kind of index. It is advisable to display the processing conditions 123 of the target wafer additionally on the screen.

Figure 14A:
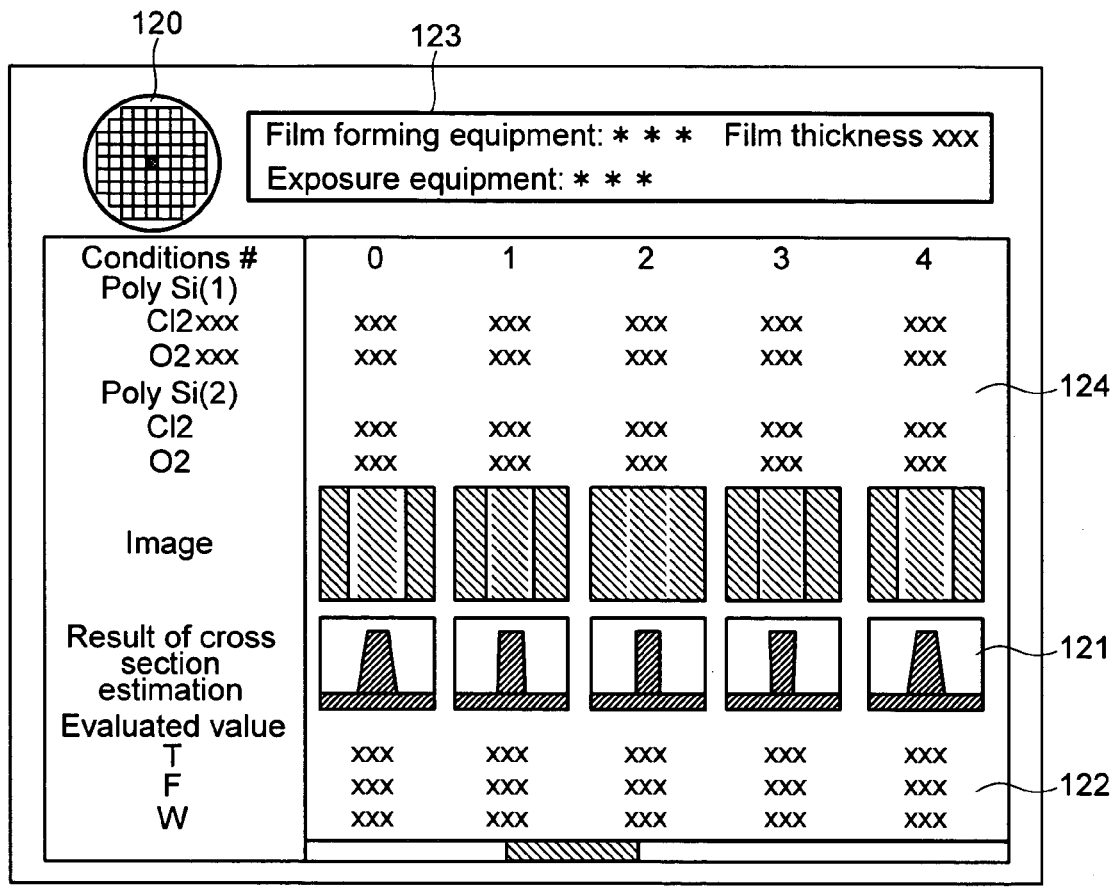
FIG. 14A is a diagram which shows a display method of acquisition results of information of three dimensional shapes of plural wafers.

Moreover, at the time of optimum condition finding, plural wafers are processed and shapes are compared between these wafers. In that case, as shown in FIG. 14A, it is effective to display an estimated value of the cross section of each wafer along with its processing conditions in a column. In FIG. 14A, pattern evaluation results at a chip location on the wafer map 120, shown in the upper left insert, among several wafers each having different etching conditions, are shown in a side-by-side arrangement. In FIG. 14A, the result of cross section estimation 121 and the information of a three dimensional shape 122 are displayed along with the etching conditions 124 of each wafer. At this time, if they can be re-arranged in a sequence on the basis of the main parameter specified by the operator, information that is more useful could be obtained.

Figure 14B:
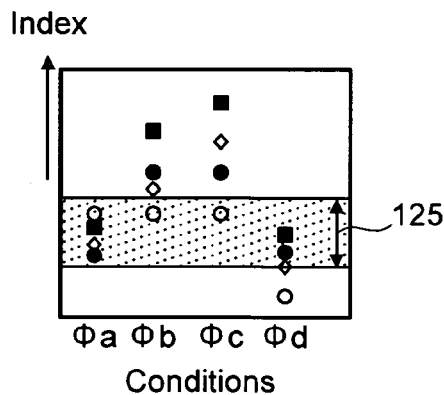
FIG. 14B is a diagram which shows a wafer dependency display method.
Figure 14C:
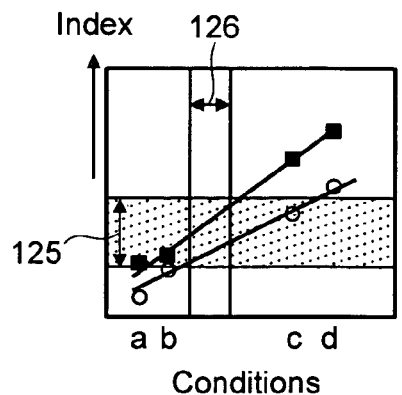
FIG. 14C is a diagram which shows an etching condition dependency display method.

As shown in FIG. 14B, the following display may be allowed: an evaluation result of a three dimensional shape for a set of parameters ($\Phi_x(x=a-d)$ represents a set of parameters of a certain etching condition) is graphically displayed; the index is displayed with a main parameter among them represented in the horizontal axis, as shown in FIG. 14C; and the like. Meshed sections in FIG. 14B and FIG. 14C indicate a target range 125 of the three dimensional shape. In particular, if it is displayed as in FIG. 14C, the operator can estimate roughly the etching conditions 126 for providing the desired shape. As shown in FIG. 14B and FIG. 14C, a display method in which different marks are used for different locations in the wafer is also effective.

As described above, the use of the invention makes it possible to acquire information of a pattern cross section easily and fast. In particular, the invention enables shape evaluation that makes clear the influence of each step and that the conventional measuring system could not support, hence enabling the efficiency of the optimum etching condition finding to be improved.

The cross sectional observation that has been practiced in the conventional optimum condition finding not only requires much time, but also requests the operator to command a technique different from that required in operating etching equipment, such as preparation of a specimen and acquisition of cross sectional SEM photographs. On the contrary, since shape evaluation according to the invention can be automatically performed using an SEM in a production line, any one can evaluate the shape in a short time. Since a large number of locations in a wafer or in a chip can be measured without difficulty, a distribution in a chip or in a wafer can be grasped easily.

Furthermore, since the specimen is not subjected to damage at the time of shape evaluation, the wafer can proceed to processing of the subsequent process if an excellent shape has been obtained.

In addition, according to the invention, since variation in the pattern shape caused by alteration of the processing conditions can be evaluated quantitatively, it becomes easy to set processing conditions that realize desired conditions, and, hence, optimization of the conditions can be carried out efficiently.

Note that, in the example, the slope angle, the flaring, and the pattern width are used as indexes. However, if the distance between the inside peak and a point on the ground level is measured, it can be used as an index indicating the roundness of the pattern top part as well. Since the shape to be controlled according to each process differs, what is necessary is just to use these indexes in combination as needed. For example, consider a case where the pattern top part is rounded in order to improve the capability of being embedded. In Si etching in a device isolation process, the roundness of the top part can be used as an effective index.

Next, a second embodiment will be described. In the first embodiment, the human operator determines a step whose conditions need to be altered and the amounts of alteration of processing conditions based on a pattern cross section estimated by SEM images. In the second embodiment, alteration of these conditions is performed automatically.

In this embodiment, first, main pattern shape indexes and adjustment parameters of the processing conditions in each step that corresponds to them are specified in advance. As a pattern shape index, a target value and a tolerance value are set up and stored. Next, a wafer for finding optimum conditions is subjected to etching, a pattern shape is evaluated using SEM images, and processing condition adjustment parameters that have been specified in advance are altered based on a difference between the measured value and the target value. Then, processing, evaluation, and modification are repeated. This procedure is repeated until the pattern shape comes to the target shape.

A procedure for finding optimum etching conditions that is a major part of the second embodiment will be described with reference to FIG. 1. In this embodiment, first, the wafer is subjected to the following process under appropriate initial conditions: an etching process consisting of BARC etching (Process 1001), Poly Si etching (1) (Process 1002), and Poly Si etching (2) (Process 1003); and a resist removal process (Process 1004) consisting of ashing and washing; and a pattern is formed thereon. Next, the measuring SEM 200 is used to acquire electron beam images of a circuit pattern after the etching (Process 1005), and subsequently a pattern cross section is evaluated using the electron beam images (Process 1006). Since this procedure of acquiring the electron beam images with SEM and processing the images is the same as that of the first embodiment, its explanation will be omitted.

Then, based on obtained results of shape evaluation, the quality of the pattern shape is evaluated in the light of differences between shape indexes and target values (Process 1010). If an excellent shape is not obtained, a step whose conditions are to be altered is determined and new conditions are set up based on obtained information of a three dimensional shape (Process 1011). Here, the relationship between each index of the shape and a corresponding step and its target value shall be referred to on the basis of what has been stored in the storage device 301 in advance (details will be described later). A different wafer is processed under newly set-up etching conditions (Process 1012) and evaluated using SEM images, and, further, other conditions are set up; this procedure is repeated until a target shape is obtained.

By way of example, a case where the etching time of BARC etching is used as a main etching parameter affecting the top-part wiring width will be described. First, the operator sets up a main parameter used in controlling the top-part wiring width W and a target value.

Figure 15A:
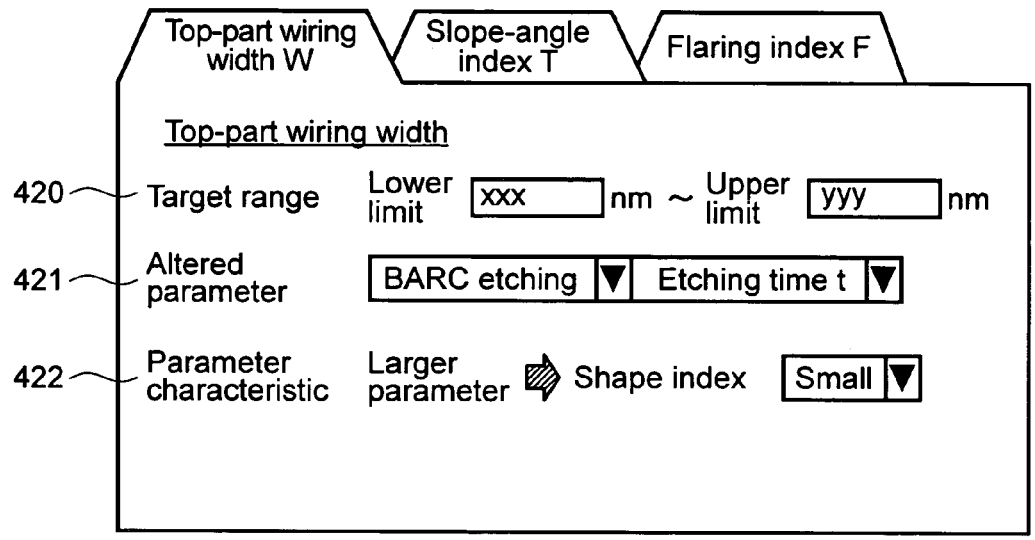
FIG. 15A is a diagram which shows a GUI screen on which etching condition parameters corresponding to various shape indexes in the second embodiment of the invention are set up.

FIG. 15A shows an example of a setting screen. A target range 420 of the top-part wiring width W is set up by a lower limit and an upper limit, first. Then, the etching time of BARC etching is selected as an altered parameter 421. At this time, the parameter that can be altered is designated as selectable suitably according to a step. If a qualitative tendency is known about this selected parameter (with an increasing parameter, how the index will vary), its parameter characteristic 422 has been specified in advance. In addition to the data of FIG. 15A, initial values of the etching conditions along with other conditions, such as a range in which each parameter can be altered, have been stored in the storage device 301. Although, in the example of FIG. 15A, only a condition of the BARC etching time is set up for the top-part width, shape indexes according to the targeted final shape and parameters that may affect respective shapes shall be used appropriately. Naturally, it is all right to consider a synergistic effect of plural processing parameters for a single shape index.

Figure 15B:
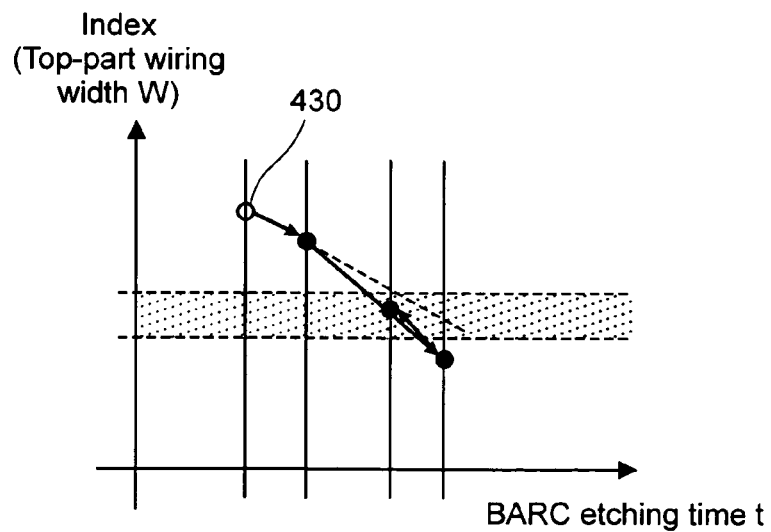
FIG. 15B is a diagram which shows an etching condition setting method.

Next, the etching process is performed using the initial conditions, and the shape index measured from the SEM image is compared with the target range. In this example, the top-part wiring width is compared with the target value being set in FIG. 15A. If the comparison with the target value indicates that the present shape is outside the target range, a new condition will be set up. FIG. 15B is an explanatory diagram of how the condition is altered. As shown in FIG. 15B, if the shape index that is an initial value 430 takes a value larger than the target value, what is necessary is to set up a value that would make the shape index smaller as the next processing condition. At this time, in the case where the parameter characteristic 422 has been set up in FIG. 15A, the next parameter is set up according to that characteristic. In the case of FIG. 15, since a characteristic that a larger etching time t will lead to a narrower top-part width W is known, the etching time is set larger than the initial condition, and the processing of the next wafer is performed. Here, if the parameter characteristic 422 is unknown in the first condition alteration, the characteristic will become clear after the condition alteration is performed in the first run. Therefore, it does not matter, although there is a possibility that the number of processings will increase by unity.

Based on the result of the etching performed in this way, the second or later condition alteration is performed as follows. Representing the initial condition by t (0), the top-part width for t (0) by W (0), the etching time after i-th condition alteration by t (i), and the top-part width for t (i) by W (i), the set value of the (i+1)-th etching time can be set up by the following formula.

$$t(i+1)=(Wt-W(i))*(t(i)-t(i-1))/(W(i)-W(i-1))+t(i), \quad \text{(Formula 4)}$$

where Wt denotes the target value (mean of the lower limit and the upper limit) of the shape index. Thus, the next processing condition is set up from the difference between the result of shape evaluation and the target value, and processing and evaluation are repeated until the target shape is obtained. In conjunction with FIGS. 15A and 15B, the top-part width and the etching time have been explained, and condition setting can be done similarly for other shape indexes and etching condition as well.

Thus, since the shape evaluation method according to the invention enables quantitative evaluation of the difference in the three dimensional shape of the pattern, optimum condition finding can be performed automatically for each shape index by having set a parameter used in controlling a particular shape corresponding thereto.

All of the processes of optimum condition finding may be preformed automatically. Alternatively, the following may be adopted: first, automatic setting of the processing condition and processing are repeated several times, and then the operator performs detailed finding of the optimum conditions based on the result. If the given parameters are not appropriate, there is a case where the shape after the processing will not converge into a target range. Therefore, it is advisable to set an upper limit to the number of condition alterations and to configure the apparatus to issue a warning when the actual number exceeds the value. Here, the etching conditions ($\Phi_{BARC}$, $\Phi_{P1}$, $\Phi_{P2}$) of FIG. 1 represent a group of the etching parameters of each step. The steps of condition determination in FIG. 15 are represented by functions f ($\Delta$W, $\Delta$T, $\Delta$F), g ($\Delta$W, $\Delta$T, $\Delta$F), and h ($\Delta$W, $\Delta$T, $\Delta$F) in a simple and easy way. Although the processes 1005 and 1006 are performed on the SEM 200 in FIG. 1, data processing other than image acquisition (Process 1005) may be performed on either the SEM 200 or the etching equipment 600, or it may be performed on a computer other than them. It is preferable that these pieces of equipment are connected with one another through a network.

Thus, in the second embodiment, the parameters can be automatically set up based on the results of quantitative evaluation of the pattern shape. In particular, since condition alteration is carried out based on shape evaluation corresponding to the steps in the etching process, it becomes possible to improve the efficiency of optimum etching condition finding. For this reason, in addition to the effect common to the first embodiment, the second embodiment has an advantage in that any operator can find optimum etching conditions fast and easily.

Figure 16:
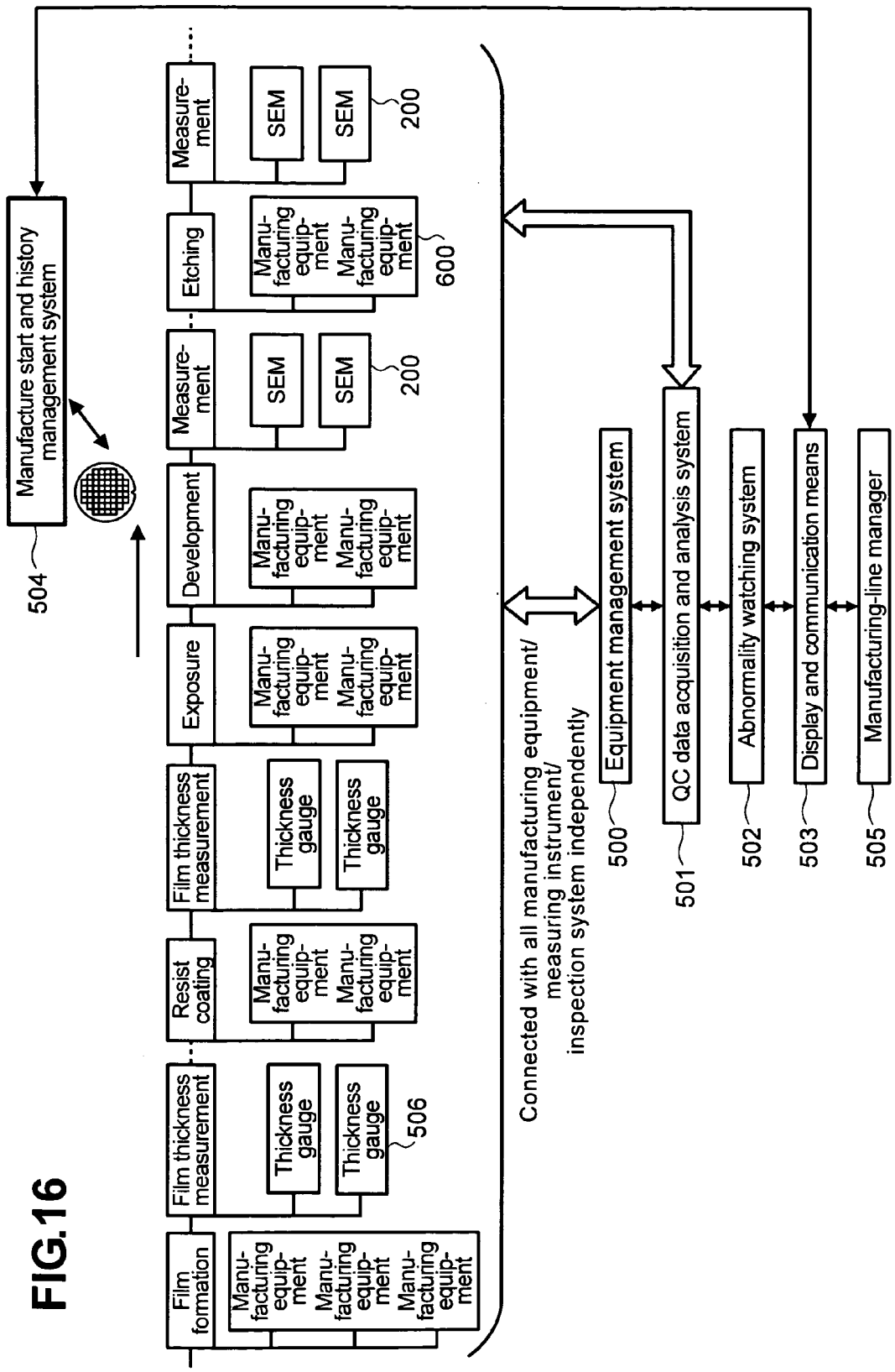
FIG. 16 is a diagram which shows an example of the construction of a semiconductor production line according to a third embodiment of the invention.

Next, a third embodiment will be described with reference to FIG. 16 and FIG. 17. With the use of information of a three dimensional shape acquired from the SEM image by the method explained in conjunction with the first and second embodiments, the state of the process can be watched in a production line. FIG. 16 shows an example of the construction of a production line to which the invention is applied. Each manufacturing equipment is connected to an equipment management system 500 through a network. The equipment management system 500 manages information of device kinds, manufacturing conditions of processes, etc. as well as operating states and maintenance situations of these pieces of equipment. Measuring instruments, such as a thickness gauge 506 and the measuring SEM 200, are connected to a QC data acquisition and analysis system 501, which collects and manages results of thickness and measurement. This QC data acquisition and analysis system 501 is connected to an abnormality watching system 502; and, if any abnormality occurs in the measurement results, a manufacturing-line manager 505 is informed of it through display and communication means 503. Information regarding when, in which process, and by which equipment each wafer begins to be processed is managed by a manufacture start and history management system 504. This system enables the operator to refer to all wafers in process and the finished, if needed. Provided that the production line is such, for film thickness information to be used at the time of estimating the cross section, a value of the present wafer can be surely used.

Figure 17:
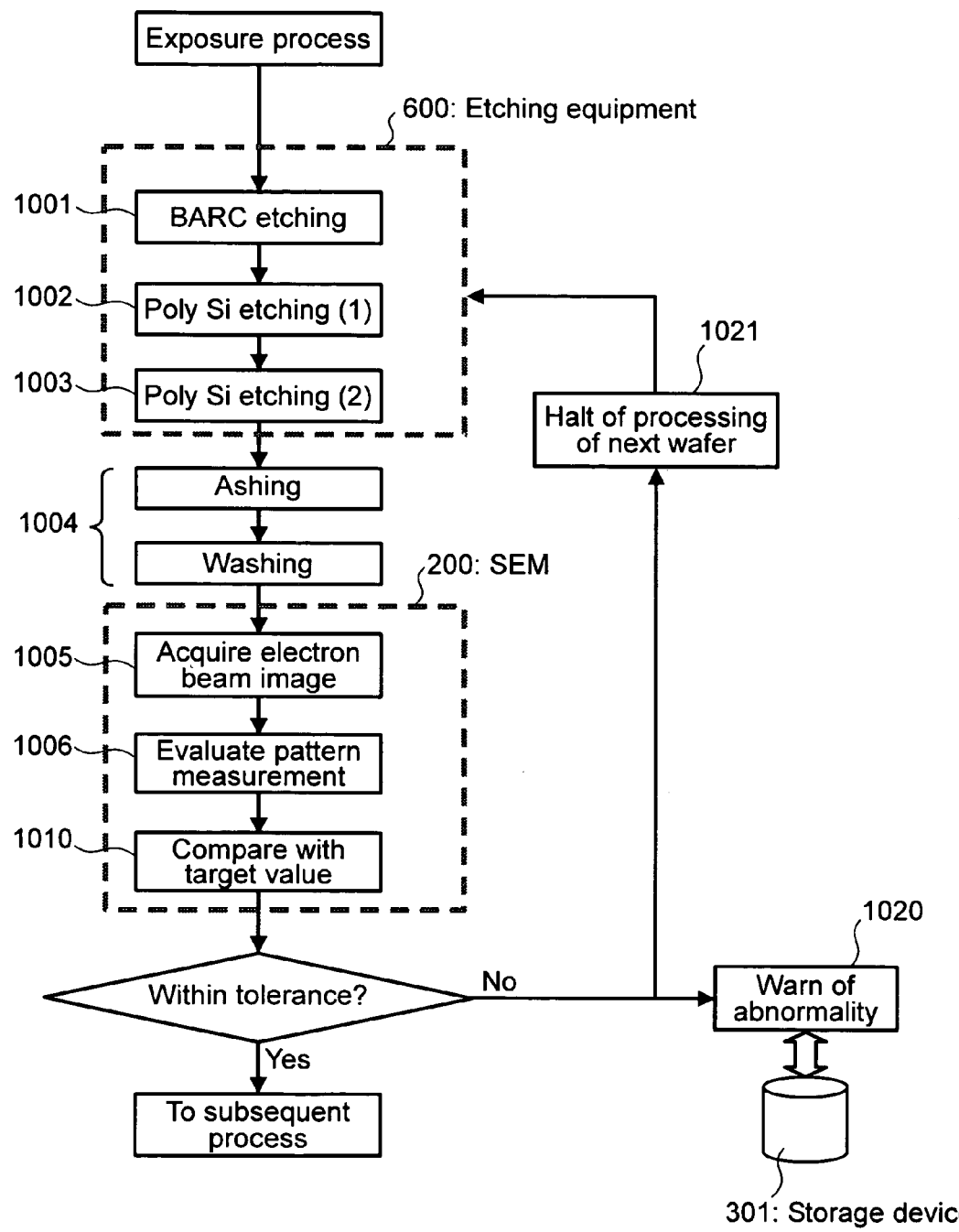
FIG. 17 is a flow diagram which shows an etching process monitor method in the third embodiment of the invention.

FIG. 17 shows an example of an embodiment of an etching process watching system according to the invention. In a production line in which the process watching is conducted, tolerances for pattern shape, such as pattern wiring width, slope angle, and flaring, have been set up in advance. These set values are recorded in the storage device 301. In the production line, a pattern on the wafer that has undergone etching (Processes 1001–1003) and ashing and washing (Process 1004) is evaluated using SEM images (Processes 1005 and 1006). Since the procedure for acquiring electron beam images by SEM and processing the images is the same as that of the first embodiment, an explanation thereof will be omitted here. The information of a three dimensional shape of the pattern obtained from the SEM image is compared with the target value and tolerance (Process 1010). If it exceeds the tolerance, a warning of an abnormality is communicated to a line manager (Process 1020) using communication means (503 of FIG. 16), and subsequent processing of the wafer is interrupted (Process 1021). At this time, if both the pattern shape exceeding the tolerance and the etching step corresponding to it are displayed, the operator can easily find at which step the problem occurred, enabling rapid action against it. It is recommendable to register this information of the etching step corresponding to a defective pattern shape in advance and record it in a storage device, as shown in the second embodiment. The second embodiment allows the operator to monitor the shape variation in a wafer or in a chip, as with the first embodiment.

The shape evaluation of the invention can be automatically performed using an SEM in the production line. Thus, by watching the three dimensional shape of a pattern using the shape evaluation system of the invention, abnormalities of the etching process can be found at an early stage, and production of a device that may include a defect can be prevented. In particular, the invention can perform such shape evaluation corresponding to steps in the etching that the conventional measuring system could not support, enables rapid investigation of a cause, and thereby makes it possible to increase the operating ratio of the etching equipment. Since the invention can measure a large number of points in a wafer or in a chip, the distribution in the wafer and in the chip can be grasped without difficulty.

Next, a fourth embodiment will be described with reference to FIG. 18. In conjunction with the first and second embodiments, the method of acquiring information of a three dimensional shape from an SEM image and the method of finding optimum etching conditions based on the obtained information of a three dimensional shape were explained. In the course of the optimum etching condition finding like this information of a relationship between the processed shape and the etching condition in each step, as shown in FIG. 15B, can be collected. If this relationship between the processed shape and the etching condition is recorded as part of a database, an excellent processed pattern shape will be able to be maintained constantly by altering processing condition parameters in response to variation in the etching condition even after the production has begun.

Figure 18:
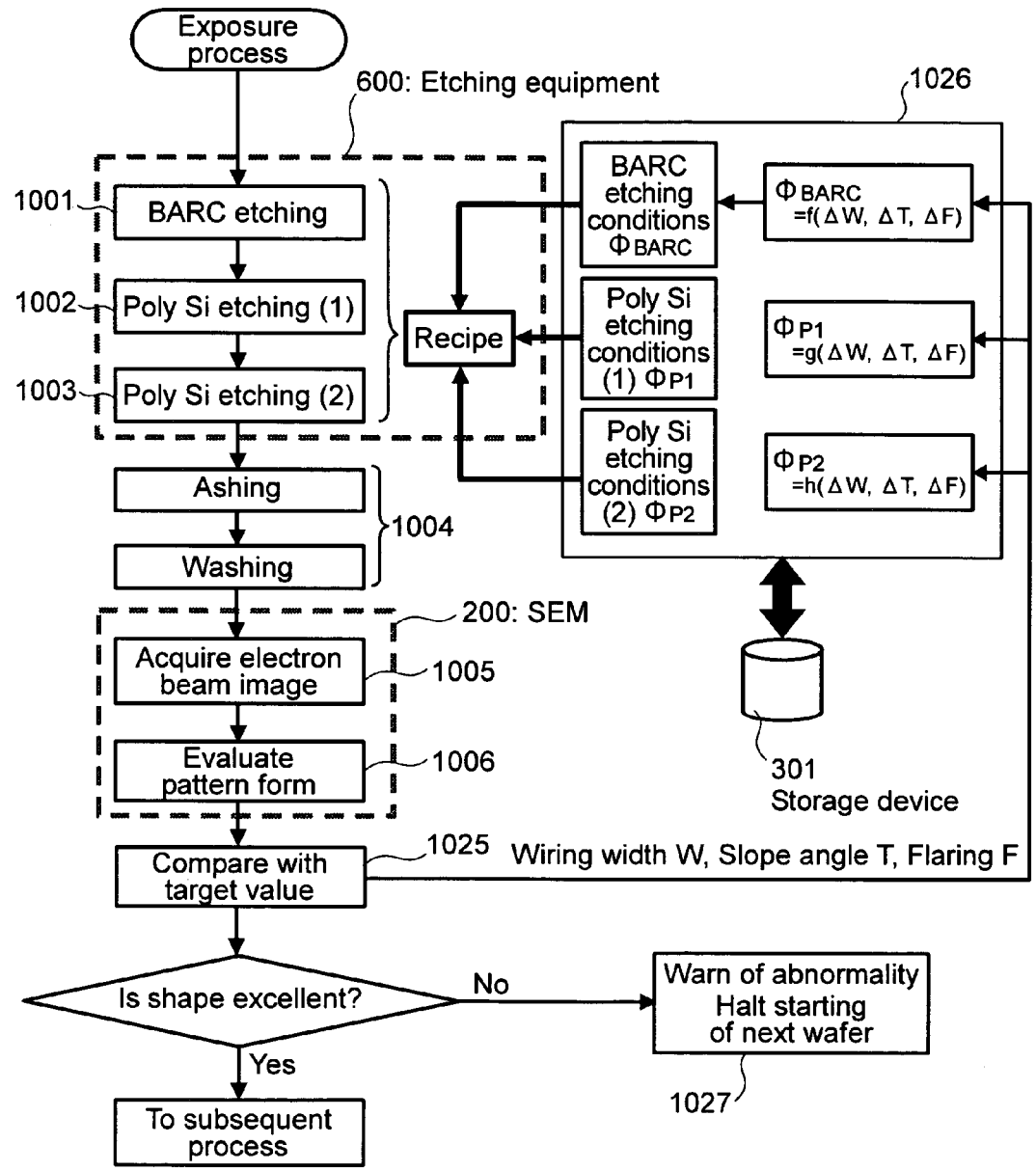
FIG. 18 is a flow diagram which shows an etching process control method in a fourth embodiment of the invention.

FIG. 18 shows the flow of the etching process control according to the invention. As with the third embodiment, the wafer is made to undergo a complete set of etching process (Processes 1001–1003) and ashing and washing (Process 1004), and the pattern after the processing is evaluated using SEM images (Processes 1005 and 1006). The information of a three dimensional shape obtained in this way is compared with the target value (Process 1025), and this result is used to investigate a relationship between the pattern shape and the etching condition parameters in advance. A processing condition that corrects the shift quantity of the pattern shape from the desired shape is calculated from the relationship thus calculated (Process 1026). At the time of the processing of the next wafer, the processing can be performed using these corrected processing conditions. For subsequent wafers, a stable pattern shape can be maintained always by repeating etching, shape evaluation, and modification of the processing conditions similarly. When an abnormality exceeding the tolerance is detected from the result of shape evaluation, a line manager is informed with a warning of the abnormality using a display and communication means (503 of FIG. 16) and wafer processing thereafter is interrupted (Process 1027). At this time, if a pattern shape exceeding the tolerance and the etching step corresponding to it are displayed, the operator can easily find in which step the problem occurred, enabling rapid action against it.

Figure 19:
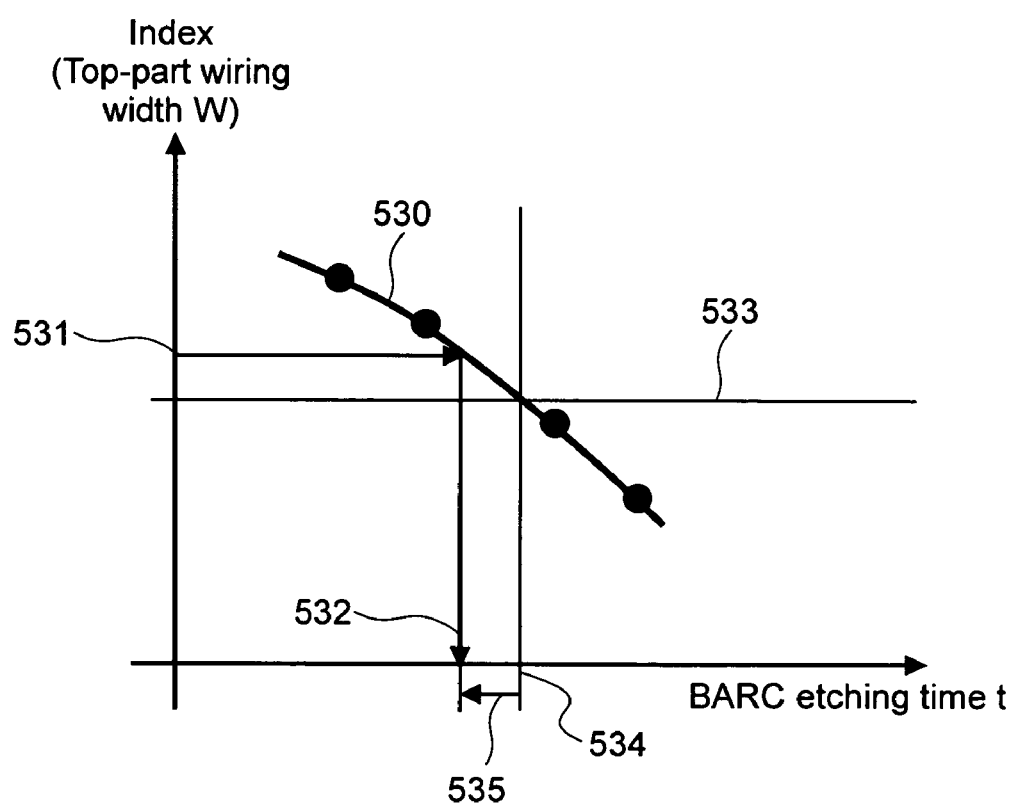
FIG. 19 is a diagram which shows an etching condition alteration quantity calculation method in the fourth embodiment of the invention.

If a model of the etching process has been established by applying a suitable function 530 to data representing a relationship between processing condition parameters obtained at the time of optimum condition finding and a pattern shape, as shown in FIG. 19, a proper modification quantity of the processing condition can be easily calculated. What is necessary next is just to set a difference between the processing condition 532 corresponding to processed shape index 531 of the present wafer and a processing condition 534 corresponding to a target shape 533 to a modification quantity 535 of the processing conditions using this function 530. FIG. 19 illustrates the relationship between the wiring width and the BARC etching time. A process for other parameters may be performed similarly.

Figure 20A:
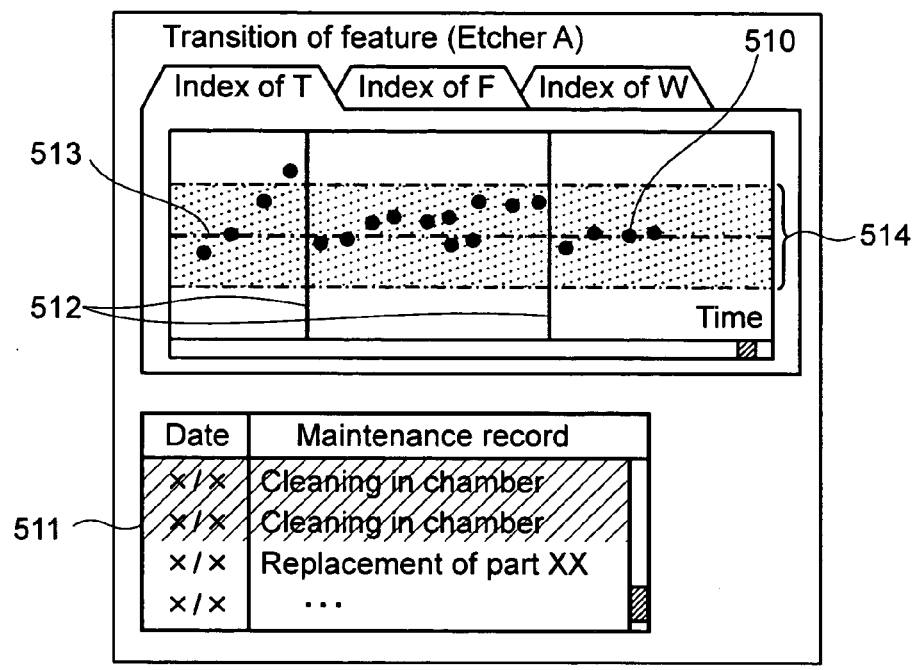
FIG. 20A is a diagram which shows one example in which the state of the etching process in the fourth embodiment of the invention is displayed in terms of transition of feature.
Figure 20B:
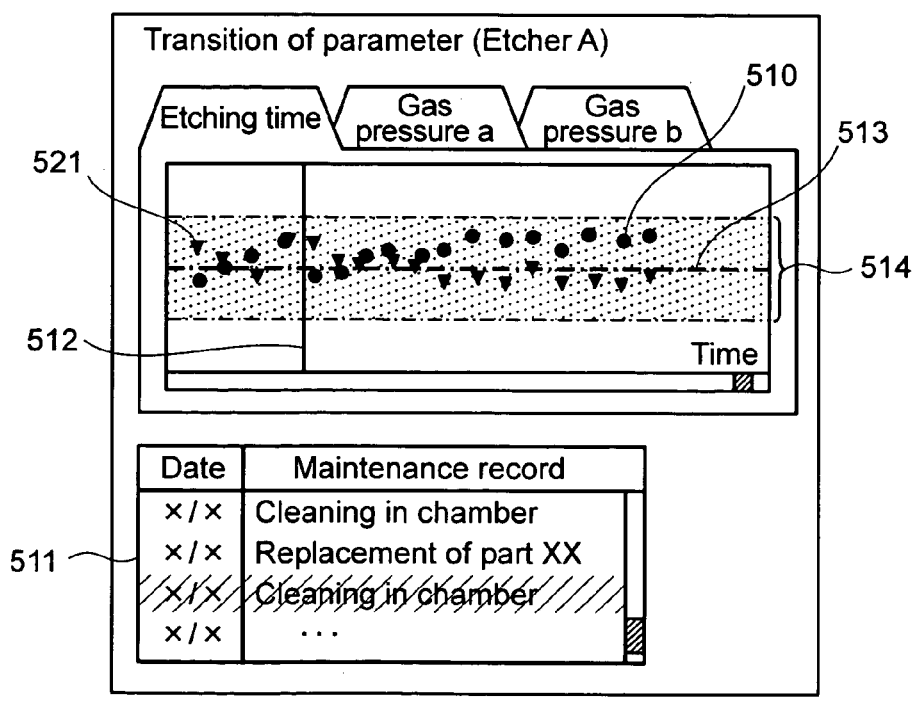
FIG. 20B is a diagram which shows one example in which the state of the etching process in the fourth embodiment of the invention is displayed in terms of the transition of a parameter.

FIGS. 20A and 20B illustrate an example of the embodiment showing obtained information on the etching process in the process control shown in FIG. 18. Because the etching equipment introduces a variation in the pattern shape due to adhesion of byproducts generated during the processing inside the chamber and the wear of parts, cleaning and replacement of parts are performed regularly. The present invention allows display of both maintenance records of the equipment and transition of information of a three dimensional shape obtained from the SEM image. As shown in FIG. 20A, the time series data 510 is graphically displayed for each piece of information of a three dimensional shape and a table of the maintenance record 511. The maintenance records in a graphical representation are displayed with the color changed, and a maintenance record display 512 is displayed so that the corresponding time can be seen on the graph. The tolerance 514 as well as the target value 513 are displayed in the time series data graph.

These displays are performed for each etching equipment. If data of the same etching equipment exists on a different measuring SEM and they are connected with one another on a network, as seen in FIG. 16, any of these pieces of data can be transferred and displayed. The reference data does not necessarily exist on the SEM, and it may be exist in another site connected to the network. The horizontal axis shall represent the time and date of the start of manufacture of the wafer, accumulated working time of the etching equipment, or other parameters corresponding to the sequence of the start of fabrication of the equipment, such as the accumulated number of wafers that were subject to fabrication on the etching equipment. Although data is shown for each piece of information of a three dimensional shape in FIG. 20A, a plurality pieces of information of the three-dimension information may be displayed simultaneously on a single graph. Alternatively, these pieces of information may be converted to a value indicating the state of the whole, such as a sum, and displayed.

Moreover, FIG. 20A shows the index for each information of a three dimensional shape, but needless to say, a variation of an etching parameter estimated from the obtained feature may be displayed, as shown in FIG. 20B. In the example of FIG. 20B, an adjustment quantity 521 is displayed along with a variation 510 of the etching condition. Adopting a display like this, the operator can easily check how much condition alteration is being executed and to what degree a variation exists that cannot be coped with in the condition alteration. Along with FIG. 20A or FIG. 20B, outputs of various sensors (pressure gauge etc.) installed in the etching equipment may be displayed. Since these sensor outputs indicate the state of the equipment at the time of processing a wafer, an effect of variation of the equipment being exerted on the pattern shape can be checked easily by displaying them simultaneously.

The shape evaluation according to the invention can be automatically performed using an SEM in a production line. Thus, an always stable etching process can be realized by detecting variation in the three dimensional shape of the pattern and controlling etching conditions so that the variations are corrected using the shape evaluation system of the invention. Especially, the invention can perform shape evaluation that corresponds to the steps of the etching process that cannot be supported by the conventional measuring system, having an advantage that control can be performed while paying attention to a step where the process variation occurred.

Next, a fifth embodiment will be described with reference to FIG. 21. The description of the first through fourth embodiments was directed to cases where only SEM images observed from the top were used. In the fifth embodiment, a method of acquiring information of a three dimensional shape using a tilt image will be described.

Figure 21:
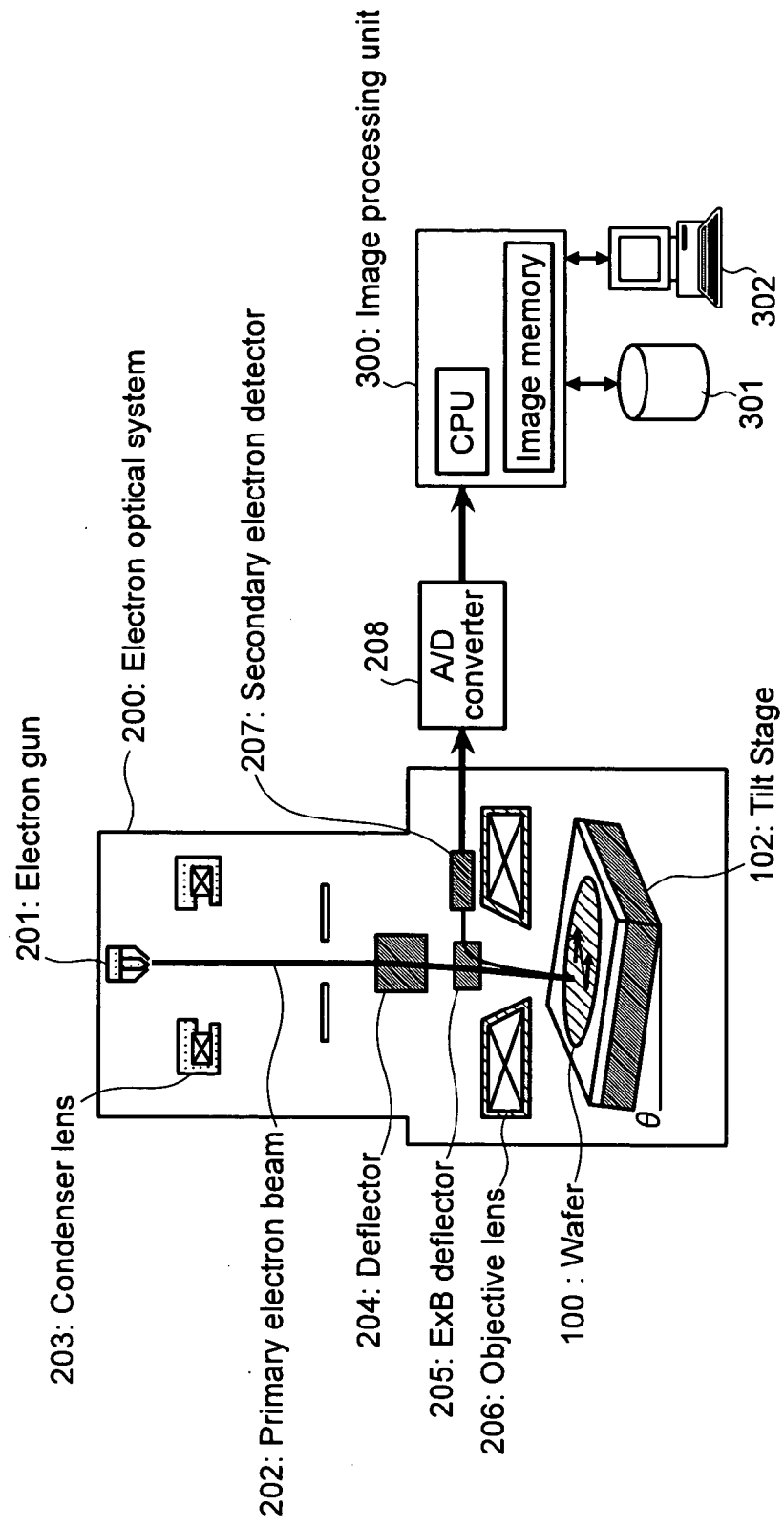
FIG. 21 is a diagram which shows the overall configuration of an SEM having a stage tilting function according to a fifth embodiment of the invention.

As shown in FIG. 21, a CD-SEM used in this embodiment has a tilt stage 102 that is movable in a XY plane and is further equipped with a tilt function, which enables a tilt image to be obtained besides a normal top-down view image.

Figure 22:
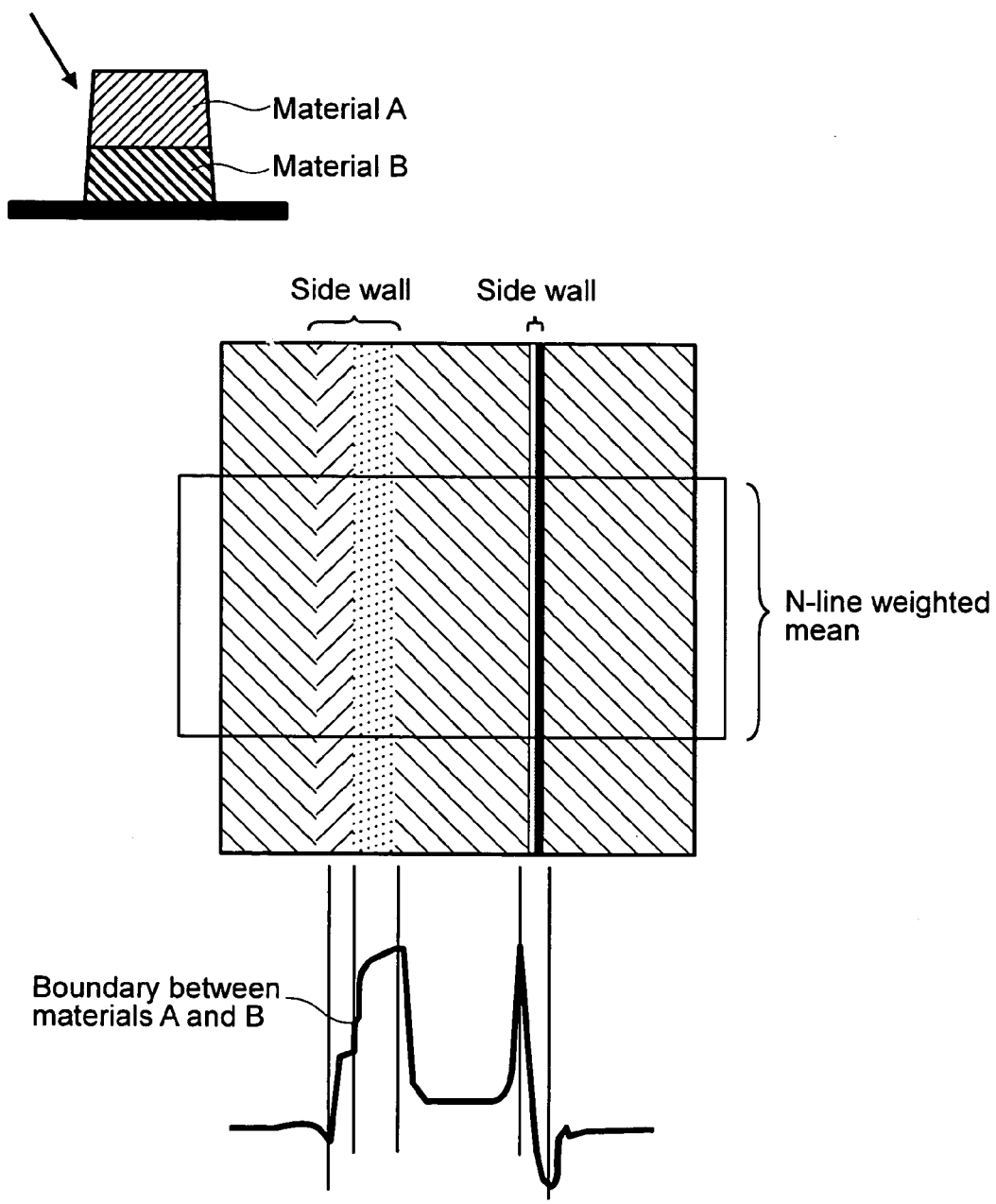
FIG. 22 is an explanatory diagram showing a method of acquiring information of a three dimensional shape by tilt images according to the fifth embodiment of the invention.

In the tilt image, a part corresponding to a left-hand resist side wall has an increased number of pixels and a part corresponding to a right-hand resist side wall has a decreased number of pixels (in the case where the inclination of the tilt stage is upward to right with respect to a specimen). What should be considered in this embodiment is a line profile of the part corresponding to the resist side wall of the side having the increased number of pixels. If the slope plane of the side wall can be detected to a sufficient width, since the edge effect and the influence of beam resolution can be avoided, a more accurate shape index can be obtained. In the case of a multilayer film in which a number of different kinds of films, such as ploy-metal gate, are laminated, the top-down view image has a fewer number of pixels corresponding to the side wall, and consequently detection of its boundary position is difficult. With the use of the tilt image, as shown in FIG. 22, the boundary can be detected easily. If the boundary position of the multilayer film was successfully detected, a pattern cross section can be estimated based on information of each film thickness, as with the first embodiment. Also, in the case of a multilayer film, the etching conditions are switched over according to the material of the film; therefore, optimum condition finding and process control can be performed based on its three dimensional shape, as with the first through fourth embodiment.

Figure 2C:
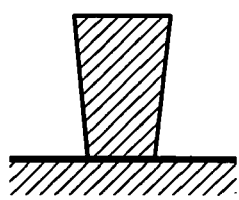
Figure 2D:
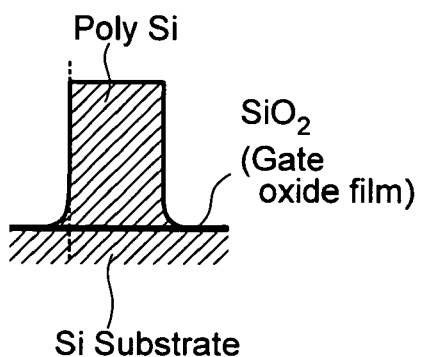

Moreover, with a top-down view, it is difficult to distinguish the downward taper shown in FIG. 2C from a normal pattern. However, offset can be added to the index of the slope angle by tilting and, consequently, detection of the downward taper becomes possible. It is also effective in detection of notches generated at the pattern bottom.

In this embodiment, the CD-SEM can acquire a tilt image, as well as a normal top-down view image, and it can calculate the height of the pattern by a principle of stereoscopy.

The cross section estimation method explained in conjunction with the first embodiment uses information of film thickness. However, in the case where there is not a film acting as a stopper, such as an element isolation process, it is necessary to a detect variation of an etching rate. In this embodiment, since the absolute height of the pattern can be detected directly, such a process can be supported.

Incidentally, instead of tilting the stage, a column of the electron optical system may be tilted, or the incident angle of the irradiating electron beam onto the specimen may be changed by changing its deflection angle.

If three dimensional shape evaluation of this embodiment is used in combination with any one of the first through fourth embodiments, more accurate shape information can be obtained in addition to the same effect explained hitherto in conjunction with these embodiments, because the use of tilt images increases the number of pixels corresponding to the side wall. More accurate optimum condition finding and process control becomes possible. Measurement of the downward taper, which is impossible to measure with top-view, becomes possible for a certain range of taper.

Next, a sixth embodiment will be described with reference to FIG. 23. In conjunction with the first through fourth embodiments, cases where only SEM images observed from the top were explained, and in conjunction with the fifth embodiment, a method of combining tilt images was explained. In conjunction with the sixth embodiment, a method of acquiring information of a three dimensional shape by using a reflection electron images will be described.

Figure 23:
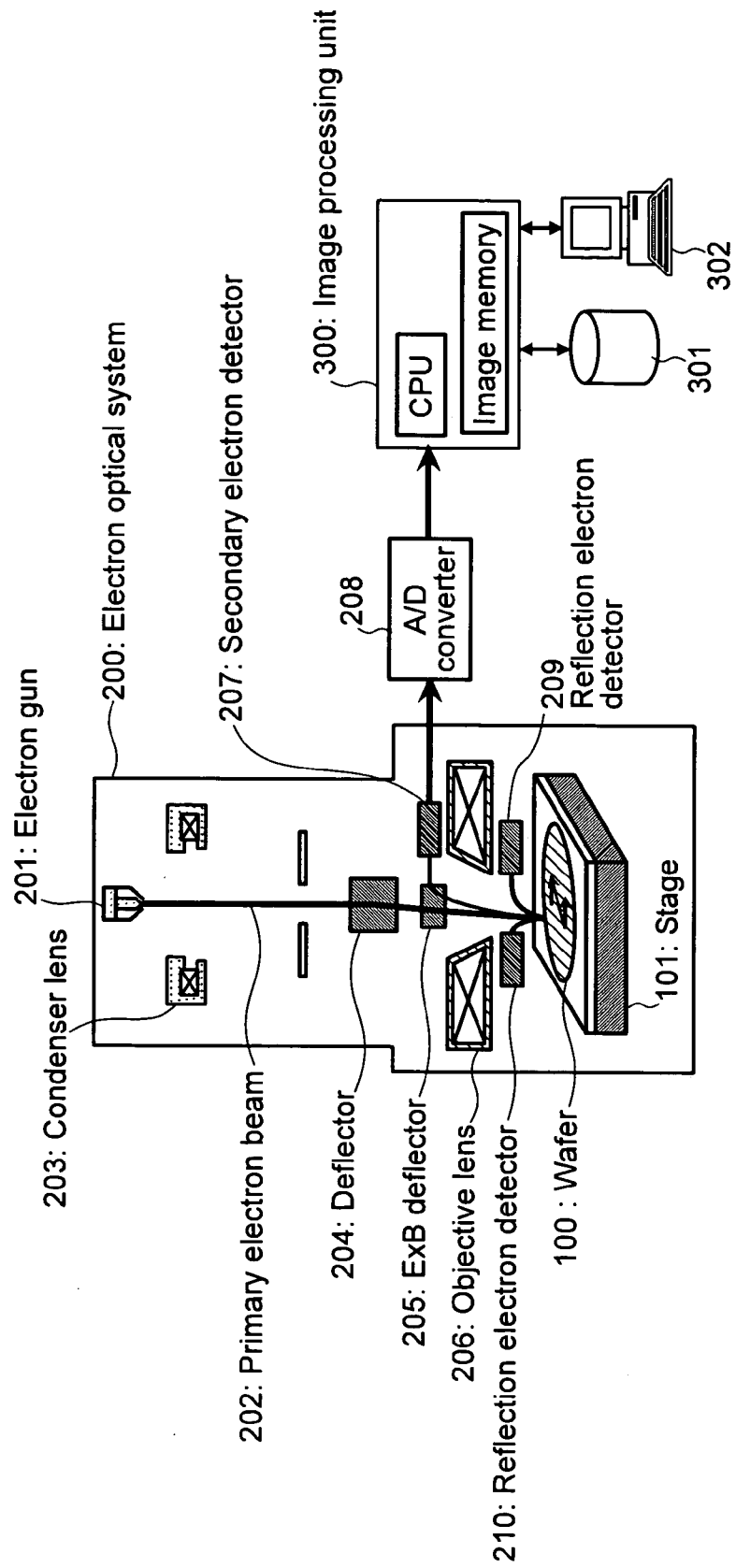
FIG. 23 is a diagram showing the overall configuration of an SEM having a reflection electron detecting function according to a sixth embodiment of the invention.
Figure 24A:
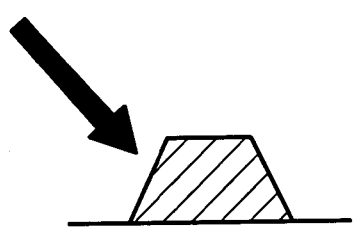
FIG. 24A is a diagram, for the sixth embodiment of the invention, showing a reflection electron image (shadow image) obtained when the electron beam is irradiated onto the pattern from a side of the arrow.
Figure 24A:
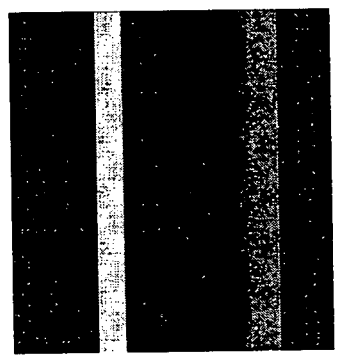
Figure 24B:
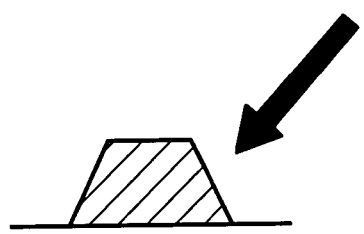
FIG. 24B is a diagram which shows a reflection electron image (shadow image) obtained when the electron beam is irradiated onto the pattern from a side of the arrow that is opposite to the arrow in FIG. 24A.
Figure 24B:
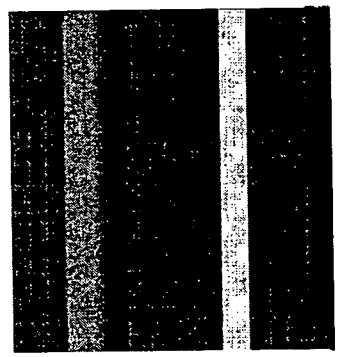

The CD-SEM used in this embodiment has reflection electron detectors 209, 210, as shown in FIG. 23, which are capable of obtaining shadow images, as shown in FIG. 24A and FIG. 24B, in addition to normal top-down view images. After acquiring such a shadow image, the degree of inclination of the edge part of the pattern is calculated from the shadow image, which is used in combination with the shape index used in the first embodiment to perform more accurate estimation of the slope angle.

Moreover, since the reflection electron has strong dependency on the kind of material as compared to the secondary electron, it becomes possible to cope with a multilayer film in which a number of different kinds of films are laminated using this characteristic. Generally, in the reflection electron image, the signal quantity is known to change depending on atomic numbers of a target object. Therefore, not only the difference in the slope angles but also the difference in materials causes the signal quantity to change. Then, as with the fifth embodiment, if the line profile is divided according to a boundary of materials, paying attention to this change in the signal quantity, it is also possible to estimate a pattern cross section, as with the first embodiment, based on information of film thicknesses of the materials. Also, in the case of a multilayer film, the etching condition is switched according to the material of each film, and, consequently, optimum condition finding and process control based on the three dimensional shape can be performed as with the first through fourth embodiments.

The height of the pattern and a feature of the side wall may be obtained using a tilt image also for the reflection electron image, as with the fifth embodiment.

With the use of these embodiments in combination with any of the first through fourth embodiments, in addition to the same effect as described in the foregoing, more accurate optimum etching condition finding and process control in the etching process will be able to be performed, because of the addition of information of the slope intensity on the pattern edge part.

Next, an embodiment of a method of displaying information of a three dimensional shape of the pattern obtained using the pattern shape evaluation technique of the invention will be described with reference to FIG. 25A through FIG. 31B.

With the use of the pattern shape evaluation technique of the invention according to the first embodiment, the image of the side-wall section of the pattern, as shown in FIG. 9, can be evaluated after being divided into regions of a high slope-angle section, a flaring section, etc. In order to check the state of the etching process easily, it is necessary to display the state intelligibly using these pieces of information.

Figure 25A:
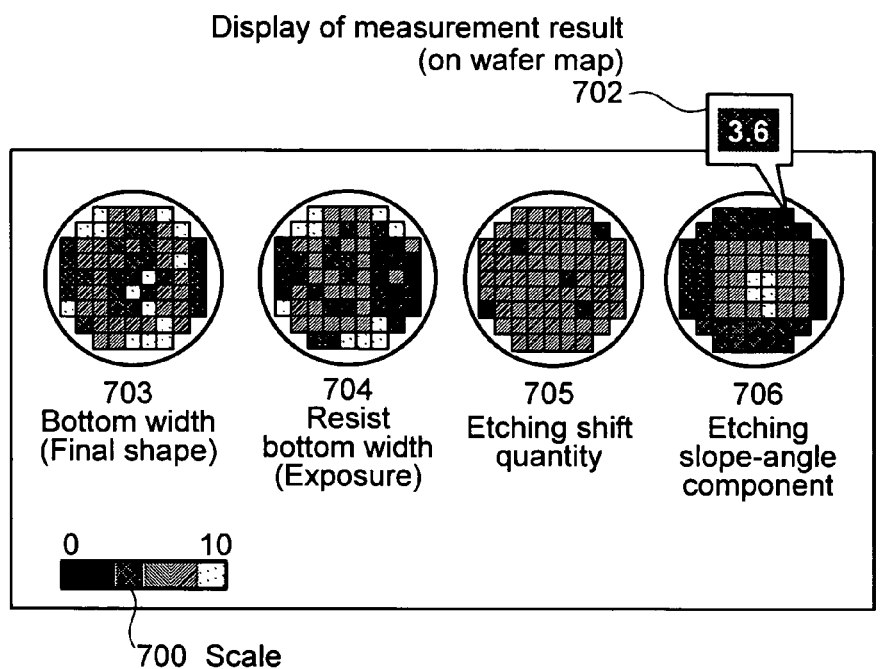
FIG. 25A is a diagram which shows a measurement result display method of a seventh embodiment of the invention, and FIG. is a diagram which 25B shows a pattern cross section before and after the etching.
Figure 25B:
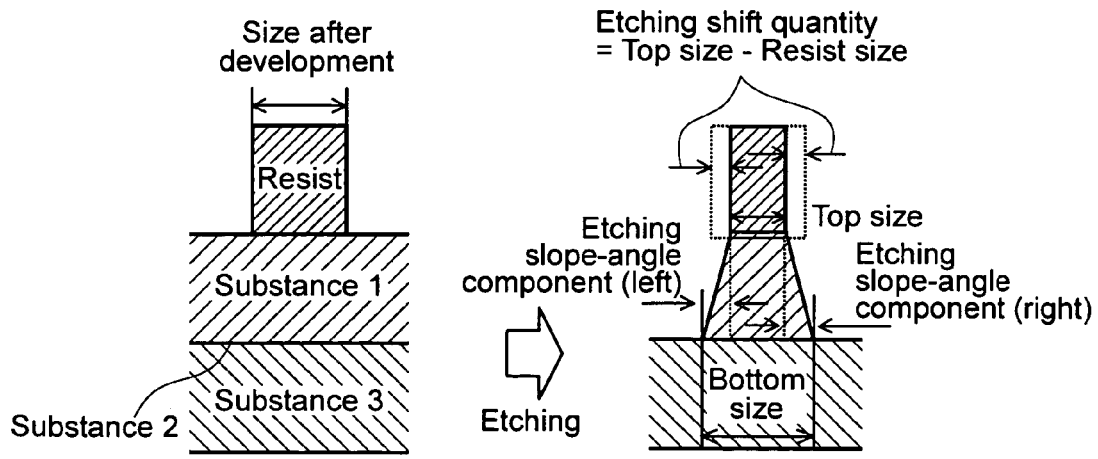

First, a seventh embodiment (map representation of variation components in exposure and etching) will be described with reference to FIGS. 25A and 25B. FIG. 25A shows an example of display of results, which involves a display method that is effective in evaluating a three dimensional shape after the etching and in judging which step in the exposure and etching processes caused shape fluctuation in the wafer plane. As shown in FIG. 25B, the bottom size after the etching depends on a combination of the following: a resist pattern size before the etching; a change in the resist pattern size acting as a mask during the etching process; a difference in the processed shape of the side wall in the etching process (taper etc.); and the like. Because each variation has a different cause, if the degree to which each parameter varies is known, it will be convenient to determine the process parameters to be adjusted. In the embodiment, the evaluation results of chips are represented in a wafer map view as seen in FIG. 25A. For example, each rectangle corresponding to a chip in the wafer map is colored according to a value of the evaluation result and is displayed. At this time, if a scale 700 indicating which range of values is represented by each color is displayed simultaneously, it is convenient. It is preferable that ranges and increments of the scale 700 are set to be modifiable appropriately. In addition to colors in the map, a figure of the evaluation result is written on each rectangle corresponding to each chip additionally (measurement result display 702).

The leftmost wafer map in FIG. 25A shows a distribution of a bottom width 703 of the final pattern after the etching. This variation in the final bottom width is generated from a combination of processes from a resist pattern formation by exposure to completion of etching. Then, if wafer maps of a resist bottom width 704, an etching shift quantity 705, and an etching slope-angle component 706 are displayed side by side, as shown in FIG. 25A, it becomes possible to easily check on which part the shape fluctuation causes the bottom width variation in the final shape.

Here, the etching shift quantity represents a difference between the top size after the etching and the size of an etching mask (in the case of FIGS. 25A and 25B, the resist mask), as shown in FIG. 25B, and mainly depends on the etching resistance (selectivity of mask substance) of the mask. This top width can be calculated by subtracting a slope-angle component that will be described below from the bottom width.

Moreover, as shown in FIG. 25B, the etching slope-angle component represents a length equivalent to a projection of the side wall on the wafer plane, and it is equal to the sum of right and left slope-angle indexes in the first embodiment. This component represents the slope of the side wall of the pattern after the etching, and the shape of the side wall depends mainly on the anisotropy in the etching. The right and left etching slope-angle components are components constituting the bottom width of the final pattern. When the bottom width varies, these elements must be varied respectively.

If the pattern evaluation technique of the invention is used, variation of each component can be evaluated after the variation in the shape has been broken down into components. As described above, each component of the shape variation corresponds to an etching characteristic (selectivity of mask and anisotropy) and arises at a particular step corresponding to its processing. Therefore, once the variation is found, it becomes possible to set the etching conditions for providing the desired shape. Even when the variation in the final shape is small, there is even a case where the variations cancel each other out and each variation of the shape component is large. According to this embodiment, a situation like this can be checked by comparing these wafer maps.

Here, in order to check the ratio of the evaluation results easily, it is preferable that results to be compared mutually are displayed in the same scale. In the example of FIGS. 25A and 25B, it is advisable that the apparatus is configured in such a way that the same kind of quantity is displayed in the same scale in the wafer maps of the resist bottom width, the etching shift quantity, and the etching slope-angle component.

In the example of FIGS. 25A and 25B, although results of chips all over the wafer are displayed, all the chips do not always need to be measured, and, naturally, only results of measured chips may be displayed. As shown in FIG. 25A, all the maps may be displayed on a single screen, or the apparatus may be configured to allow each map to be selected by a button operation etc. In the case where much more information of the pattern shape can be obtained by using a tilt image etc. as provided in the fifth embodiment, it is recommendable to add a wafer map of an important shape component appropriately besides the shape components of FIG. 25A.

Thus, by displaying the evaluation results obtained by the pattern shape evaluation system in a wafer map view and by displaying variations of shape after breaking it down into components, it becomes possible to easily check information useful to estimate a cause of the shape variation. In the case where the variation in the pattern shape is extremely minute, it is difficult to judge a distribution in the wafer plane only by evaluating a few patterns because there is an influence of noises at the time of shape measurement. In the shape evaluation using the conventional cross sectional SEM images, there is a case where variation in the shape cannot be checked with evaluation of five points or so in the wafer plane. However, if the shape variation is displayed in the form of a wafer map, as shown in FIG. 25A, even if the measurement results are accompanied with some noise, how the shape varies in the wafer plane can be judged from an overall trend.

Next, an eighth embodiment (map representation of an etching variation component) will be described with reference to FIG. 26. In the seventh embodiment, a method of displaying a size variation resulting from the exposure process and a size variation resulting from the etching process simultaneously has been explained. In the eighth embodiment, an example of displaying a fluctuation component resulting from only the etching process will be described.

As shown in FIGS. 3A–3E, even when the etching is etching performed in a single piece of equipment, in actual practice, the processing is performed as a combination of several steps in may cases. Then, as shown in FIG. 26, there is even a case where information, that is useful to set the conditions in the etching process and control it, can be obtained by displaying only a size variation component resulting from the etching process, as with the seventh embodiment.

Figure 26:
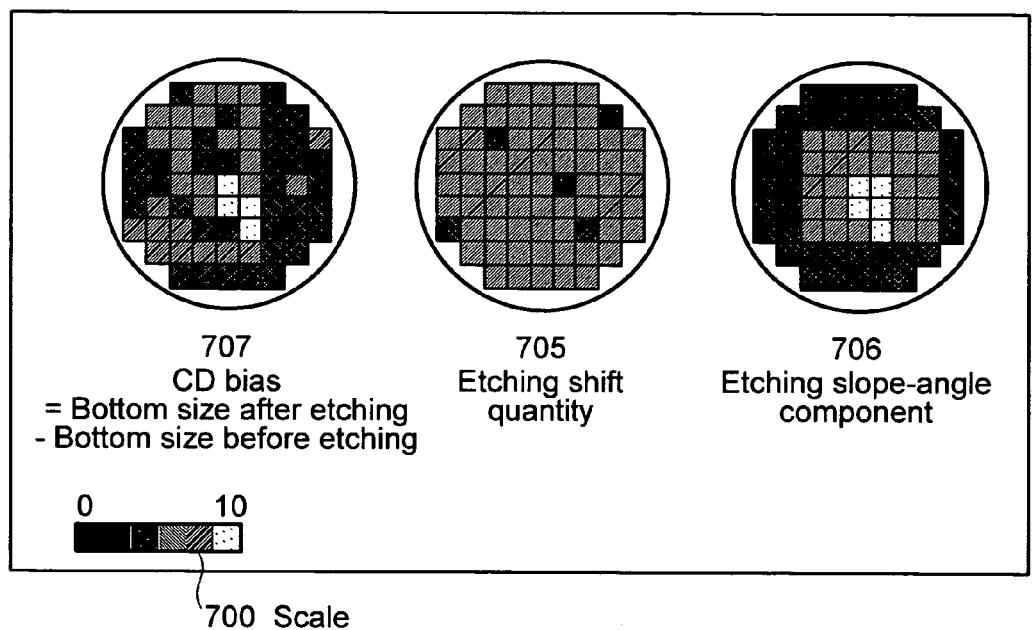
FIG. 26 is a diagram which shows a measurement result display method of the eighth embodiment of the invention.

The leftmost wafer map in FIG. 26 represents a measurement result of a CD bias 707. The CD bias represents a difference of the bottom width before and after the etching, being equal to the measurement result of the bottom width of FIG. 25B after subtracting the measurement result of the resist bottom width therefrom. This quantity indicates a shape fluctuation generated only in the etching process from which the influence of shape fluctuation in the exposure process is excluded. The central and right-hand wafer maps display the etching shift quantity 705 and the slope-angle component 706, separately, as breakdowns of this shape fluctuation. Thus, by displaying the shape variation in the etching process after breaking it down into components, how the shape fluctuation resulting from the etching arises can be checked easily.

As shown in FIGS. 3A–3E, each shape component stems from a different step. For example, variation in the side-wall slope angle is mainly caused by variation in etching anisotropy in Step 1 in FIG. 3C. In the light of this and other similar facts, the method makes clear a step to which a countermeasure should be taken according to the shape. Therefore, with the use of the result display method of this embodiment, processing conditions for providing the desired shape can be set relatively easily.

Also, in this embodiment, as with the seventh embodiment, it is preferable that the results to be compared mutually are displayed in the same scale in order to easily check the ratio of the evaluation results. All the chips do not always need to be measured, and, naturally, only results of measured chips may be displayed. As shown in FIG. 26, all these maps may be displayed on a single screen simultaneously, or each map may be selected to be displayed by a button operation etc.

Thus, by displaying the evaluation result obtained by the pattern shape evaluation system in a wafer map view and by displaying variations of shape after breaking it down into components, it become possible to easily check information useful to estimate the cause of a shape variation. If the shape variation is displayed in the form of a wafer map, as shown in FIG. 26, even if the measurement results are accompanied with some noise, how the shapes vary in the wafer plane can be judged from the overall trend.

Next, a ninth embodiment (map representation for each material of multilayer film) will be described with reference to FIGS. 27A and 27B. In the seventh embodiment, the method of displaying the size fluctuation resulting from the exposure process and the size fluctuation resulting from the etching process simultaneously have been explained; and, in the eighth embodiment, the example of displaying the shape fluctuation in the etching for each component was explained. In the ninth embodiment, as shown in FIG. 22, the shape fluctuation is displayed for each evaluation result of each layer based on the pattern evaluation results of a multilayer film.

Figure 27A:
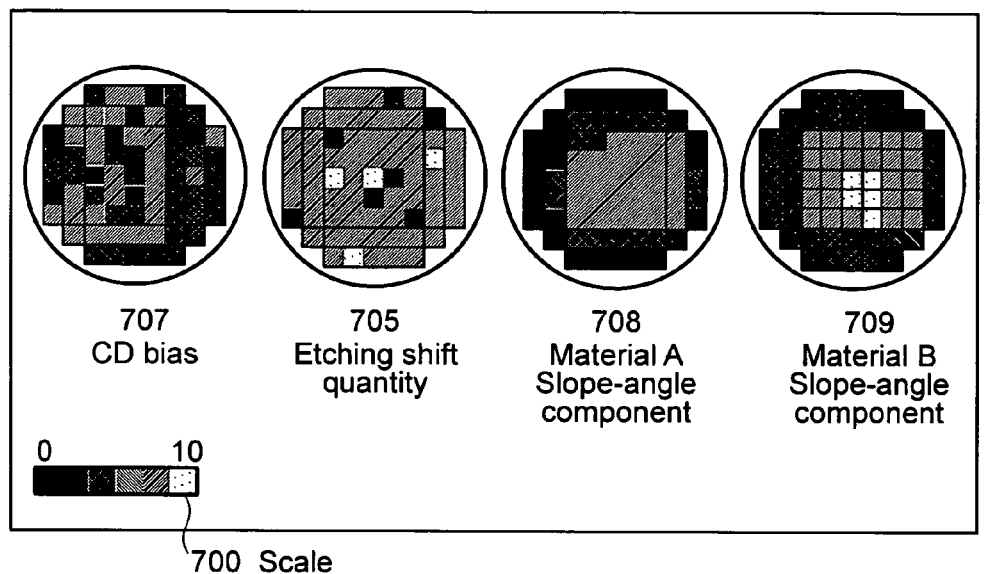
FIG. 27A is a diagram which shows a measurement result display method according to a ninth embodiment of the invention.
Figure 27B:
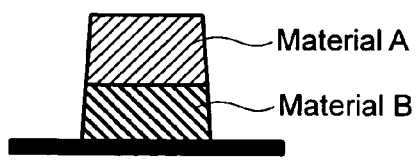
FIG. 27B is a sectional view of the pattern.

In the case of etching of a multilayer-structured sample, as shown in FIG. 27B, normally different etching conditions are used according to the material of each layer. Therefore, by displaying the result of each object layer in this way, it becomes possible to easily check a step that causes shape fluctuation to be large. Although only two materials are displayed in FIG. 27B, if the sample has much more layers, naturally, a layer to be displayed may be added. In FIG. 27A, only the etching shift quantity 705 and slope-angle components 708 (material A) and 709 (material B) for respective materials are displayed. However, for example, evaluation of the material B may be performed by further breaking it down into the slope-angle component and the flaring component, and these results may be displayed together.

Also, in this embodiment, as with the seventh and eighth embodiments, it is preferable that the results to be compared mutually are displayed in the same scale in order to easily check the ratio of the evaluation results. All the chips do not always need to be measured, and, naturally, only results of measured chips may be displayed. As shown in FIG. 27A, all of these maps may be displayed on a single screen simultaneously, or each map may be selected to be displayed by a button operation etc.

Thus, by displaying the evaluation result obtained by the pattern shape evaluation system in a wafer map view and by displaying variations of shape after breaking it down into material-specific components, as shown in FIG. 27A, it becomes possible to easily check information useful to estimate the cause of a shape variation. If the shape variation is displayed in the form of a wafer map, as shown in FIG. 27A, even if the measurement results are accompanied with some noise, how the shape varies in the wafer plane can be judged from the overall trend.

Figure 28:
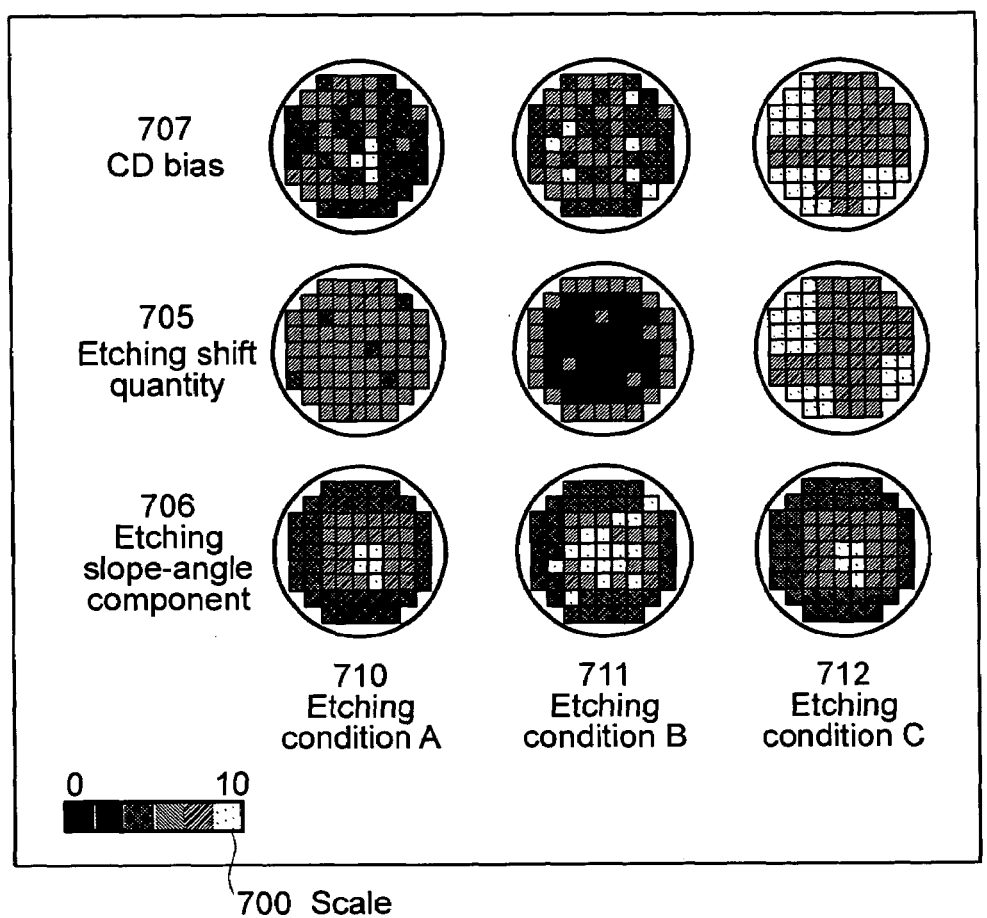
FIG. 28 is an explanatory diagram showing a measurement result display method representing a tenth embodiment of the invention.

Next, a tenth embodiment (map representation for optimum etching condition finding) will be described with reference to FIG. 28. In the tenth embodiment, an example of a display method, in which display of the seventh through ninth embodiments is used for optimum etching condition finding, will be described. If wafer maps equal to those in, for example, the eighth embodiment are assigned to one group and several groups of wafer maps are arranged and displayed in columns for respective etching conditions, as shown in FIG. 28, size variation and a situation of variation of each component in the wafer plane can be checked easily in the optimum etching condition finding; therefore, which etching condition among 710 etching condition A, 711 etching condition B, and 712 etching condition C is excellent can be checked easily. In the example of FIG. 28, although the same wafer maps as those of the eighth embodiment were displayed, naturally, wafer maps of the seventh embodiment or the ninth embodiment may be used.

In order to check a ratio of the evaluation results easily in this embodiment as with the seventh through ninth embodiments, it is preferable that the results to be compared mutually are displayed in the same scale. All the chips do not always need to be measured, and, naturally, only results of measured chips may be displayed. The apparatus may be configured to allow all of these maps to be displayed on a single screen simultaneously, as shown in FIG. 28, or to allow these maps to be switched on a component basis by a button operation etc.

Efficient finding of the optimum etching condition becomes possible in this way, by displaying the evaluation result obtained by the pattern shape evaluation system in a wafer map view according to the etching condition and by displaying variations of shape after breaking it down into material-specific components, as shown in FIG. 28. If the shape variation is displayed in the form of a wafer map, as shown in FIG. 28, even if the measurement results are accompanied with some noise, how the shape varies in the wafer plane can be judged from the overall trend.

Next, an eleventh embodiment (map representation for displaying aging) will be described with reference to FIG. 29. In the eleventh embodiment, a technique for displaying the aging of the etching state intelligibly will be described. Generally, in etching equipment, the etching characteristic may vary because by-products generated during the etching adhere on the inside of it's the etching chamber or because parts wear. Then, in a relatively excellent state just after cleaning of the etching equipment and replacement of parts, the pattern shape after the etching and the variation thereof in the wafer plane are evaluated and recorded, and a change in the state is checked appropriately, whereby the necessity of the next cleaning and replacement of parts can be judged.

Figure 29:
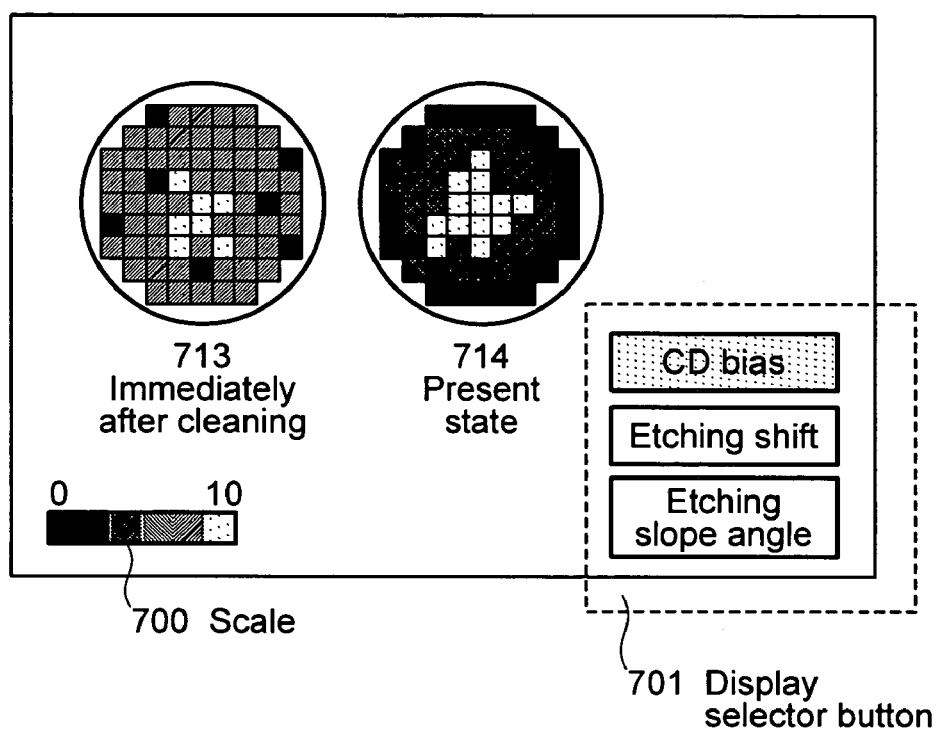
FIG. 29 is an explanatory diagram showing a measurement result display method representing an eleventh embodiment of the invention.

Then, for example, if the evaluation result immediately after the cleaning of the etching equipment 713 and the evaluation result of the present condition (the latest state) 714 are displayed side by side, as shown in FIG. 29, the situation of the aging of the equipment can be checked easily. The example of FIG. 29 illustrates an example in which the same wafer maps as those in the eighth embodiment are switched by a display selector button 701 and displayed. The wafer maps of all the shape components may be displayed on a single screen. Needless to say, wafer maps that use shape components in the seventh or ninth embodiment may be used.

In addition, in this embodiment, it is preferable that, as with the seventh through ninth embodiments, the results to be compared mutually are displayed in the same scale in order to easily check the ratio of the evaluation results. All of the chips do not always need to be measured, and, naturally, only results of measured chips may be displayed. Instead of this embodiment, results of evaluating processed results by different etching equipment may be arranged and displayed. Thereby, a difference in the processed result between different equipment can be checked easily.

Thus, by displaying the evaluation result obtained by the pattern shape evaluation system in a wafer map view according to the etching condition and by displaying a variation of shape as compared with the previous state, as shown in FIG. 29, a change of state of the etching equipment can be checked easily. If the shape variation is displayed in the form of a wafer map, as shown in FIG. 29, even if the measurement results are accompanied with some noise, how the shape varies in the wafer plane can be judged from the overall trend.

Incidentally, if an effective shape component can be separated and measured besides the shape components shown in the seventh through ninth embodiments, naturally wafer maps of the components may be displayed together. For example, if the tilt image etc. is used, as shown in conjunction with the fifth embodiment, further information of the side wall of the object pattern can be obtained, and, consequently, a still newer component can be set.

Figure 30:
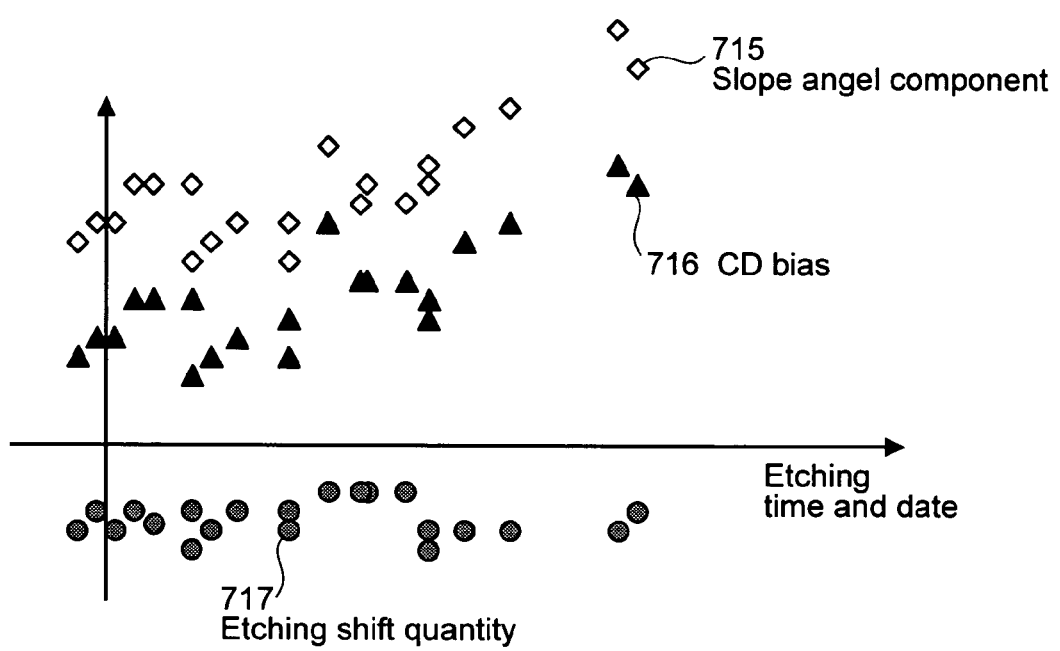
FIG. 30 is an explanatory diagram showing a measurement result display method representing a twelfth embodiment of the invention.

Next, a twelfth embodiment (graphical representation for displaying aging) will be described with reference to FIG. 30. In the twelfth embodiment, another technique for displaying aging of the etching state intelligibly will be described. In the eleventh embodiment, variation in the pattern shape was displayed in the form of a wafer map; in the twelfth embodiment, the variation is displayed graphically. As shown in FIG. 30, shape variation components (715 a slope-angle component, 716 a CD bias, 717 an etching shift quantity) that are displayed in respective wafer maps in the embodiments described in the foregoing are now represented in a single graph, each component group of data forming one series.

FIG. 30 shows an example using the results of shape evaluation of the eighth embodiment. The horizontal axis of the graph represents time and date when the etching was performed, and the vertical axis represents each component of the evaluation results. If the shape variation of the etching pattern is displayed for each component as a graph of time variation in this way, the situation of the aging of the etching equipment can be checked easily. In FIG. 30, one group of evaluation results is plotted for one round of etching, but it may be replaced with a typical value representing the state of the processed wafer. For example, the value is a mean of five points in the wafer. In order to display a situation of variation in the wafer plane, a standard deviation may be plotted in addition to the mean value. Alternatively, a graph may be prepared for each point in the wafer plane, and graphs thus prepared may be arranged on the screen. In the example of FIG. 30, although the same evaluation result components as those in the eighth embodiment were displayed, naturally the evaluation result components in the seventh or ninth embodiment may be used.

Thus, by displaying the evaluation results obtained by the pattern shape evaluation system graphically so that variation of each component can be recognized, a change of state of the etching equipment can be checked easily. Since a shape component that varies is made clear, a parameter to be modified in order to improve the etching state can be determined relatively easily.

Figure 31A:
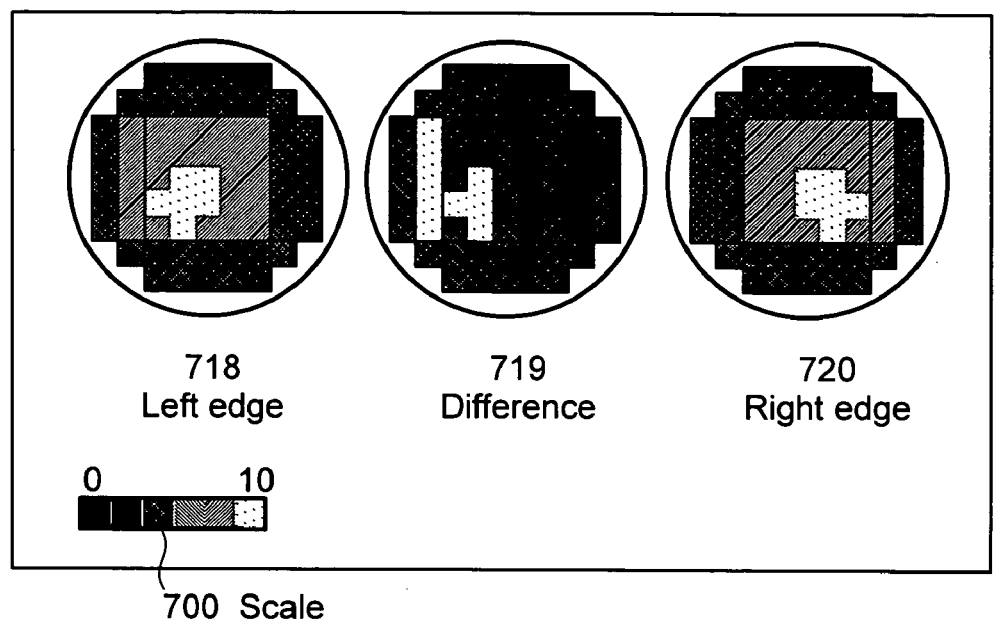
FIG. 31A is a diagram which shows an asymmetry evaluation result display method according to a thirteenth embodiment of the invention.
Figure 31B:
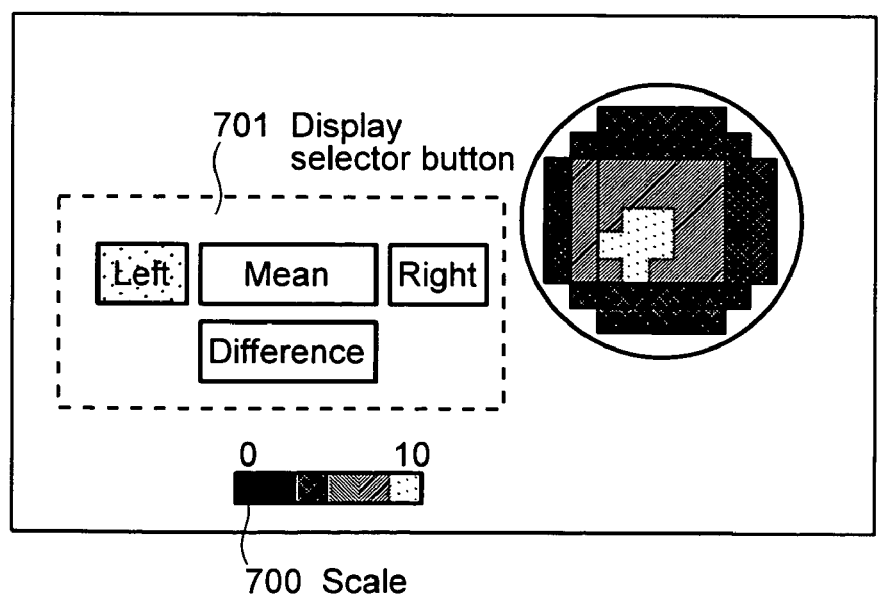
FIG. 31B is a diagram which shows an asymmetry evaluation result of the thirteenth embodiment of the invention and a display of a display selector button.

Next, a thirteenth embodiment (asymmetry wafer map representation) will be described with reference to FIGS. 31A and 31B. In the shape evaluation technique shown in the first embodiment, information of a three dimensional shape is obtained by dividing the signal waveform of the pattern edge part into several shape components. Since this information of a three dimensional shape can be calculated for the right edge and for the left edge, respectively, the asymmetry of the pattern shape having left-right asymmetry can also be evaluated. In FIG. 31A, calculated results of shape indexes obtained from the left and right edges (for example, slope-angle index) are displayed in different wafer maps, respectively, and a distribution of the difference between them in the wafer plane is also displayed together (718 a left-edge slope-angle index, 719 a difference between right and left slope-angle indexes, 720 a right-edge slope-angle index).

From these evaluation results, the shape asymmetry in the wafer plane can be checked easily. If the asymmetry of the pattern shape is extremely minute, it difficult to judge it only by evaluating one pattern, because there is an effect of noise at the time of shape measurement. However, if the shape variation is displayed in the form of a wafer map, as shown in FIG. 31A, even if the measurement results are accompanied with some noise, how the shape varies can be judged from the overall trend. FIG. 31B is another example of a display. In this example, the apparatus is configured to allow the mean to be displayed besides the right and left edges and a difference between them, and to allow a display of them to be switched by the display selector button 701.

Thus, by displaying the evaluation results of the right and left edges in a comparable form, it becomes possible to check the asymmetry of the pattern shape easily and surely. As shown in FIGS. 31A and 31B, by checking the pattern shape by displaying it in the form of a wafer map, an asymmetric distribution of pattern shape in the wafer plane can be judged stably from the overall trend even if the evaluation results are accompanied with some noise.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for inspecting a three dimensional shape, comprising:
   electron-beam irradiating means for irradiating a focused electron beam onto a specimen while scanning the electron beam;
   signal detecting means for detecting secondary electrons generated from the specimen by irradiation of the electron beam; and
   signal processing means for performing arithmetic processing on the signal from the signal detecting means; wherein
   the signal processing means has both an evaluating function of dividing the signal waveform obtained by the signal detecting means into plural regions on the basis of variation of the signal quantity and evaluating the three dimensional shape of the specimen using sizes of the divided regions, and
   a displaying function of preparing maps each representing a distribution in a wafer plane with respect to two or more kinds of shape-representing values selected from a group consisting of a size of the plural divided regions and values obtained by summing or subtracting the sizes of the plurality of the divided regions, and displaying these wafer maps in arrangement or in a switch-selectable manner.

2. The apparatus according to claim 1, wherein
   the displaying function displays wafer maps of an evaluation value representing a three dimensional shape of the specimen before and after etching of an etching process.

3. The apparatus according to claim 1, wherein the displaying function displays a wafer map whose display items are any one of the following sets:
   bottom width after etching, side-wall component, top width, and resist width; or
   CD bias, side-wall component, and top-width shift quantity; or
   CD bias, and side-wall components of each layer; or
   features corresponding to right and left edges, difference, and mean.

4. The apparatus according to claim 1, wherein the displaying function displays a set of evaluated results obtained under different etching conditions simultaneously.

5. The apparatus according to claim 1, wherein the displaying function displays simultaneously evaluation results of a plurality of specimens processed by the same processing equipment, under the same processing conditions, but at different times.

6. The apparatus according to claim 1, wherein the evaluating function evaluates a three dimensional shape using an image obtained by a plurality of electron beams each of which is the irradiating electron beam and forms a different angle with the specimen surface.

7. The apparatus according to claim 1, further comprising means for detecting reflection electrons generated from the spacemen by irradiation by the electron beam, wherein the evaluating function evaluates a three dimensional shape using a signal of secondary electron detected by the signal detecting means and a signal of reflection electrons detected by the means for detecting reflection electrons.

8. An apparatus for inspecting a three dimensional shape, comprising
   electron-beam irradiating means for irradiating a focused electron beam onto a specimen while scanning the electron beam;
   signal detecting means for detecting secondary electrons generated from the specimen by irradiation of the electron beam; and
   signal processing means for processing the signal from the signal detecting means, wherein
   the signal processing means is equipped with the following functions:
   a function of dividing the signal waveform obtained by the signal detecting means into a plurality of regions on the basis of a variation of signal quantity and evaluating a three dimensional shape of the specimen using sizes of the divided regions;
   a function of calculating two or more kinds of shape-representing values selected from the group consisting of the sizes of a plurality of the divided regions and values obtained by summing or subtracting the sizes of the plurality of the divided regions; and
   a function of calculating the two or more kinds of shape-representing values for a plurality of specimens processed by the same processing equipment, under the same processing conditions, but at different times, and also displaying time variations of these two or more kinds of shape-representing values graphically.

9. The apparatus according to claim 8, wherein the displaying function further displays a wafer map of evaluation values showing three dimensional shapes of the specimen before and after etching of an etching process.

10. The apparatus according to claim 8, wherein the displaying function further displays a wafer map showing any one of the following groups of display items: bottom width after etching, side-wall component, top width, and resist width; CD bias, side-wall component, and top-width shift quantity; CD bias, and side-wall components of layers; and features corresponding to right and left edges, difference, and mean.

11. The apparatus according to claim 8, wherein the displaying function further displays a group of evaluation results obtained under different etching conditions.

12. The apparatus according to claim 8, wherein the displaying function further displays evaluation results of a plurality of specimens processed by the same processing equipment, under the same processing conditions, but at different times.

13. The apparatus according to claim 8, wherein the evaluating function evaluates a three dimensional shape using an image obtained by a plurality of electron beams each of which is the irradiating electron beam and forms a different angle with the specimen surface.

14. The apparatus according to claim 8, further comprising means for detecting reflection electrons generated from the specimen by irradiation of the electron beam, wherein the evaluating function evaluates a three dimensional shape using secondary electrons detected by the signal detecting means and the reflection electrons detected by the means for detecting reflection electrons.

15. An apparatus for inspecting a three dimensional shape, comprising:
   electron-beam irradiating means for irradiating a focused electron beam onto a sample on whose surface a concavity-and-convexity pattern is formed while scanning the electron beam;
   signal detecting means for detecting secondary electrons generated from the specimen by irradiation of the electron beam; and
   signal processing means for processing a signal from the signal detecting means; wherein
   the signal processing means has both a signal processing part for obtaining information of the width and height of the concavity-and-convexity pattern formed on the specimen surface by processing the signal waveform obtained by the signal detecting means, and
   a display part for displaying the information of the width and height of the concavity-and-convexity pattern obtained by processing the signal waveform in the signal processing part.

16. The apparatus according to claim 15, wherein
the signal processing part of the signal processing means divides the signal waveform obtained by the signal detecting means into a plurality of regions on the basis of a variation of the signal quantity, and acquires information of the width and height of the concavity-and-convexity pattern formed on the sample surface using sizes of the divided regions.

17. The apparatus according to claim 15, wherein
the signal processing part of the signal processing means obtains information of the widths of a plurality of parts in the concavity-and-convexity pattern formed on the sample surface.

18. The apparatus according to claim 15, wherein
the display part of the signal processing means displays information of the width or height of the concavity-and-convexity pattern formed on the sample surface obtained in the signal processing part, the information being brought into correspondence with the pattern forming conditions of the concavity-and-convexity pattern.

19. The apparatus according to claim 15, wherein
the display part of the signal processing means displays information of a distribution in the sample surface of the width or height of the concavity-and-convexity pattern formed on the sample surface obtained in the signal processing part.

20. The apparatus claim 15, wherein
the display part of the signal processing means displays information of a distribution in the sample surface of the width or height of the concavity-and-convexity pattern formed on the sample surface that was obtained in the signal processing part, the information being brought into correspondence with the pattern forming conditions of the concavity-and-convexity pattern.

21. A method of watching an etching process, comprising the following steps of:
   etching a specimen under predetermined etching conditions;
   acquiring information of a three dimensional shape of the specimen subjected to the etching using the apparatus of claim 15 without destroying the specimen, and
   comparing the acquired information of a three dimensional shape with predetermined tolerance;
   judging the acquired information of a three dimensional shape to be abnormal if, as a result of the comparison, it exceeds the predetermined tolerance, and
   displaying information on the etching process corresponding to the information of a three dimensional shape judged to be abnormal in that case.

22. The method according to claim 21, wherein
the predetermined etching conditions under which the specimen was subjected to the etching were set based on information obtained by measuring a three dimensional shape of the specimen surface subjected to the etching under a plurality of different conditions in advance using the apparatus of claim 15.

23. The method according to claim 21, wherein
in the step of displaying information on the etching process that corresponds to information of a three dimensional shape that was judged to be abnormal on a screen, information of a three dimensional shape acquired using the apparatus of claim 15 is displayed further.

* * * * *

UNITED STATES PATENT AND TRADEMARK OFFICE
CERTIFICATE OF CORRECTION

PATENT NO. : 7,230,239 B2
APPLICATION NO. : 10/918381
DATED : June 12, 2007
INVENTOR(S) : Tanaka et al.

It is certified that error appears in the above-identified patent and that said Letters Patent is hereby corrected as shown below:

Title Page Insert

Foreign Application Priority Data

(30) Aug. 29, 2003   Japan (JP)   2003-306441

Related U.S. Application Data

(63) Continuation-in-Part (CIP) of 10/460,217, filed June 13, 2003

Signed and Sealed this

Eleventh Day of March, 2008

JON W. DUDAS
*Director of the United States Patent and Trademark Office*